(12) United States Patent
Morimoto et al.

(10) Patent No.: US 12,396,652 B2
(45) Date of Patent: Aug. 26, 2025

(54) BRAIN ACTIVITY ANALYZING APPARATUS, BRAIN ACTIVITY ANALYZING METHOD AND BIOMARKER APPARATUS

(71) Applicant: Advanced Telecommunications Research Institute International, Kyoto (JP)

(72) Inventors: Jun Morimoto, Soraku-gun (JP); Mitsuo Kawato, Soraku-gun (JP); Noriaki Yahata, Soraku-gun (JP); Ryuichiro Hashimoto, Soraku-gun (JP); Kazuhisa Shibata, Soraku-gun (JP); Takeo Watanabe, Soraku-gun (JP); Yuka Sasaki, Soraku-gun (JP); Nobumasa Kato, Soraku-gun (JP); Kiyoto Kasai, Soraku-gun (JP)

(73) Assignee: ADVANCED TELECOMMUNICATIONS RESEARCH INSTITUTE INTERNATIONAL, Kyoto (JP)

( * ) Notice: Subject to any disclaimer, the term of this patent is extended or adjusted under 35 U.S.C. 154(b) by 1834 days.

(21) Appl. No.: 16/446,332

(22) Filed: Jun. 19, 2019

(65) Prior Publication Data
US 2019/0298207 A1 Oct. 3, 2019

Related U.S. Application Data

(62) Division of application No. 14/439,145, filed as application No. PCT/JP2014/061544 on Apr. 24, 2014, now Pat. No. 10,357,181.

(30) Foreign Application Priority Data

May 1, 2013 (JP) .................................. 2013-096493

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0263* (2013.01); *A61B 5/16* (2013.01); *A61B 5/4064* (2013.01);
(Continued)

(58) Field of Classification Search
CPC ... A61B 5/7246; A61B 5/0263; A61B 5/4088; A61B 5/7264; A61B 5/16; A61B 5/4076;
(Continued)

(56) References Cited

U.S. PATENT DOCUMENTS 8,861,815 B2 10/2014 Cecchi et al.
9,101,276 B2 8/2015 Georgopoulos
(Continued)

FOREIGN PATENT DOCUMENTS

JP 2006-513742 A 4/2006
JP 2008-178546 A 8/2008
(Continued)

OTHER PUBLICATIONS

Correa et al. "Canonical Correlation Analysis for Feature-Based Fusion of Biomedical Imaging Modalities and Its Application to Detection of Associative Networks in Schizophrenia." IEEE Journal of Selected TOpics in Signal Processing, vol. 2, No. 6, Dec. 2008, pp. 998-1007. (Year: 2008).*
(Continued)

*Primary Examiner* — Angela M Hoffa
(74) *Attorney, Agent, or Firm* — BIRCH, STEWART, KOLASCH & BIRCH, LLP

(57) ABSTRACT

Provided is a method of analyzing brain activities for realizing a biomarker for neurological/mental disorder,
(Continued)

based on brain function imaging. From measured data of resting-state functional connectivity MRI of a healthy group and a patient group, correlation matrix (80) of degree of brain activities among prescribed brain regions is derived for each subject. Feature extraction is executed by regularized canonical correlation analysis (82) on the correlation matrix (80) and attributes of the subject including a disease/healthy label of the subject. Based on the result of regularized canonical correlation analysis, by discriminant analysis (86) through sparse logistic regression, a discriminator (88) is generated.

5 Claims, 13 Drawing Sheets

(51) Int. Cl.
| | | |
|---|---|---|
| A61B 5/026 | (2006.01) | |
| A61B 5/16 | (2006.01) | |
| G01R 33/48 | (2006.01) | |
| G16H 20/10 | (2018.01) | |
| G16H 30/40 | (2018.01) | |
| G16H 50/20 | (2018.01) | |
| A61B 5/369 | (2021.01) | |
| G16H 50/70 | (2018.01) | |

(52) U.S. Cl.
CPC .......... *A61B 5/4076* (2013.01); *A61B 5/4088* (2013.01); *A61B 5/7246* (2013.01); *A61B 5/7264* (2013.01); *G01R 33/4806* (2013.01); *G16H 20/10* (2018.01); *G16H 30/40* (2018.01); *G16H 50/20* (2018.01); *A61B 5/026* (2013.01); *A61B 5/0261* (2013.01); *A61B 5/369* (2021.01); *A61B 5/4848* (2013.01); *A61B 5/7267* (2013.01); *A61B 2560/0475* (2013.01); *A61B 2576/026* (2013.01); *G01R 33/4808* (2013.01); *G16H 50/70* (2018.01)

(58) Field of Classification Search
CPC ... A61B 5/4064; A61B 5/055; A61B 5/04009; A61B 5/026; A61B 5/0261; A61B 5/7267; A61B 5/04012; A61B 5/4848; A61B 2560/0475; A61B 5/0476; A61B 2576/026; G06F 19/345; G06F 19/34; G06F 19/3443; G01R 33/4806; G01R 33/4808; G01R 33/48
See application file for complete search history.

(56) References Cited

U.S. PATENT DOCUMENTS

| | | | |
|---|---|---|---|
| 9,265,441 | B2 | 2/2016 | Pereira et al. |
| 9,454,641 | B2 | 9/2016 | Cecchi et al. |
| 9,480,402 | B2 | 11/2016 | Leuthardt et al. |
| 9,510,756 | B2 | 12/2016 | Grady et al. |
| 9,612,306 | B2 | 4/2017 | Lin et al. |
| 2002/0103429 | A1 | 8/2002 | deCharms |
| 2004/0116798 | A1 | 6/2004 | Cancro et al. |
| 2005/0215884 | A1 | 9/2005 | Greicius et al. |
| 2006/0241382 | A1 | 10/2006 | Li et al. |
| 2009/0118602 | A1 | 5/2009 | Kawasaki et al. |
| 2010/0249573 | A1 | 9/2010 | Marks |
| 2012/0201320 | A1 | 8/2012 | Koike-Akino |
| 2013/0034277 | A1 | 2/2013 | Cecchi et al. |
| 2013/0116540 | A1 | 5/2013 | Li et al. |
| 2013/0231552 | A1 | 9/2013 | Grady et al. |
| 2014/0002075 | A1 | 1/2014 | Lin et al. |
| 2014/0107494 | A1 | 4/2014 | Kato et al. |
| 2014/0171757 | A1 | 6/2014 | Kawato et al. |
| 2014/0336998 | A1 | 11/2014 | Cecchi et al. |
| 2015/0018664 | A1 | 1/2015 | Pereira et al. |
| 2015/0294074 | A1 | 10/2015 | Kawato et al. |

FOREIGN PATENT DOCUMENTS

| | | |
|---|---|---|
| JP | 2011-000184 A | 1/2011 |
| JP | 2012-165370 A | 8/2012 |
| WO | WO 2006/132313 A1 | 12/2006 |
| WO | WO 2011/115956 A1 | 9/2011 |
| WO | WO 2012/165602 A1 | 12/2012 |
| WO | WO 2013/069517 A1 | 5/2013 |

OTHER PUBLICATIONS

Hardoon et al. "Unsupervised Analysis of fMRI Data Using Kernel Canonical Correlation", Neuroimage, Elsevier, vol. 37, No. 4, Sep. 14, 2007, pp. 1250-1259.

Broyd, et al. "Default-Mode Brain Dysfunction in Mental Disorders: A Systematic Review", Neuroscience and Biobehavioral Reviews 33 (2009), 279-296.

Taylor, et al. "Impact of Meditation Training on the Default Mode Network during a Restful State", Social Cognitive and Affective Neuroscience 2013 8, 4-14.

DeCharms et al., "Control over brain activation and pain learned by using real-time functional MRI", Proc Natl Acad Sci USA, vol. 102 No. 51, 18626-18631, 2005.

Kamitani et al., "Decoding the visual and subjective contents of the human brain", Nature Neuroscience, 2005; 8: 679-85.

Nikolaus Weiskopf, "Real-time fMRI and its application to neurofeedback", NeuroImage, vol. 62 (2012), pp. 682-692.

Raichle et al., "A default mode of brain function", Proc Natl Acad Sci USA, vol. 98 No. 2, 676-682, 2001.

Schönfelder, "Sparse regularized regression identifies behaviorally-relevant stimulus features from psychophysical data", The Journal of the Acoustical society of America, May 2012, vol. 131, No. 5, p. 3953-3969, Abstract.

Shibata et al., "Perceptual Learning Incepted by Decoded fMRI Neurofeedback Without Stimulus Presentation", Science vol. 334, Dec. 9, 2011.

Watanabe et al., "Greater plasticity in lower-level than higher-level visual motion processing in a passive perceptual learning task", Nature Neuroscience, 5, 1003-1009, 2002.

Advisory Action issued in copending U.S. Appl. No. 14/439,145 dated Dec. 18, 2018.

Advisory Action issued in copending U.S. Appl. No. 14/439,145 dated Nov. 27, 2018.

Anderson et al., "Functional connectivity magnetic resonance imaging classification of autism". Brain 134 (2011), pp. 3739-3751.

Baldassarre, L. et al., Structured Sparsity Models for Brain Decoding From fMRI Data. In 2nd International Workshop on Pattern Recognition in NeuroImaging 5-8 (IEEE, 2012).

Buckner, R.L., et al., "The brain's default network: Anatomy, function, and relevance to disease", Annals of the New York Academy of Science 1124, pp. 1-38, 2008.

Fukuda et al., "Decoded Neurofeedback ni yoru Seishin Shikkan Chiryo no Kanosei (Toward a Novel Treatment for Psychiatric Disorder: Review for Decoded Neurofeedback Training)," Experimental Medicine, vol. 30, No. 13 (special extra), Aug. 1, 2012, pp. 182 (2162)-187 (2167) (10 pages).

Guan, N. et al., Sparse Representation based Discriminative Canonical Correlation Analysis for Face Recognition. in 11th International Conference on Machine Learning and Applications 51-56 (IEEE, 2012).

Hampson et al., "Real-time fMRI Biofeedback Targeting the Orbitofrontal Cortex for Contamination Anxiety," Journal of Visualized Experiments, Issue 59, e3535, Jan. 20, 2012, pp. 1-10 (11 pages).

Hardoon, D. R. et al., Sparse Canonical Correlation Analysis, Machine Learning 83, 331-353 (2011).

Notice of Allowance issued in copending U.S. Appl. No. 14/439,145 dated Mar. 8, 2019.

(56) References Cited

OTHER PUBLICATIONS

Office Action issued in copending U.S. Appl. No. 14/439,145 dated Oct. 2, 2017.
Office Action issued in copending U.S. Appl. No. 14/439,145 dated Sep. 7, 2018.
Ryali, S. Sparse Logistic Regression for Whole-Brain Classification of fMRI Data NeuroImage 51, 752-764 (2010).
Shirer, W.R. et al., "Decoding subject-driving cognitive states with whole-brain connectivity patterns", Cerebral Cortex 22, pp. 158-165, 2012.
Sun, L. et al., Canonical Correlation Analysis for Multilabel Classification: A Least-Squares Formulation, Extensions, and Analysis. IEEE Transactions on Pattern Analysis and Machine Intelligence 33, 194-200 (2011).
Van den Heuvel et al., "Functionally linked resting-state networks reflect the underlying structural connectivity architecture of the human brain", Human Brain Mapping 30, pp. 3127-3141, 2009.
Van Dijk et al., "Intrinsic Functional Connectivity As a Tool for Human Connectomics: Theory, Properties, and Optimization". Neurophysiol 103 (2010), pp. 297-321.
Vounou et al., "Sparse reduced-rank regression detects genetic associations with voxel-wise longitudinal phenotypes in Alzheimer's disease," Elsevier, Neuroimage, vol. 60, No. 1, 2012 (available online Dec. 22, 2011), pp. 700-716.
Wang et al., "Extracting Multiscale Pattern Information of fMRI Based Functional Brain Connectivity with Application on Classification of Autism Spectrum Disorders", PLOS ONE 7:10, Oct. 2012, 14 pages.
Whitfield-Gabrieli, S., et al., "Default Mode Network Activity and Connectivity in Psychopathology", Annual Review of Clinical Psychology 8, pp. 49-76, 2012.
Yahata et al., "A small number of abnormal brain connections predicts adult autism spectrum disorder". Nature Communications 7:11254, Apr. 14, 2016, 12 pages.
Yahata et al., "Computational neuroscience approach to biomarkers and treatments for mental disorders". Phychiatry and Clinical Neurosciences 71 (2017), pp. 215-237.
Yamashita et al., "Sparse estimation automatically selects voxels relevant for the decoding of fMRI activity patterns," Elsevier, NeuroImage, vol. 42, No. 4, 2008 (available online Jun. 6, 2008), pp. 1414-1429.
Zotev, V. et al., "Self-regulation of amygdala activation using real-time FMRI neurofeedback", PLoS ONE 6, vol. 6, Issue 9, Sep. 2011.
Barttfeld, et al. "State-dependent changes of connectivity patterns and functional brain network topology in autism spectrum disorder", Neuropsychologia, vol. 50, No. 14, pp. 3653-3662, 2012.
Craddock et all. "Disease State Prediction From Resting State Functional Connectivity", Magnetic Resonance in Medicine, vol. 62, No. 6, 2009, pp. 1619-1628.

* cited by examiner

FIG. 12

| | OVERALL | SITE ONE | SITE TWO | SITE THREE | SITE FOUR |
|---|---|---|---|---|---|
| DISCRIMINANT PERFORMANCE | 79.3% | 83.8% | 72.0% | 84.9% | 66.2% |
| SENSITIVITY | 0.730 | 0.771 | 0.692 | | 0.529 |
| SPECIFICITY | 0.833 | 0.889 | 0.750 | 0.849 | 0.794 |
| POSITIVE LIKELIHOOD RATIO LR+ | 4.38 | 6.94 | 2.77 | | 2.57 |
| NEGATIVE LIKELIHOOD RATIO LR- | 0.324 | 0.257 | 0.410 | | 0.593 |
| DOR | 13.5 | 27.0 | 6.75 | | 4.34 |

BRAIN ACTIVITY ANALYZING APPARATUS, BRAIN ACTIVITY ANALYZING METHOD AND BIOMARKER APPARATUS

CROSS-REFERENCE TO RELATED APPLICATIONS

This application is a Divisional of copending application Ser. No. 14/439,145, filed on Apr. 28, 2015, which was filed as PCT International Application No. PCT/JP2014/061544 on Apr. 24, 2014, which claims the benefit under 35 U.S.C. § 119(a) to Patent Application No. 2013-096493, filed in Japan on May 1, 2013, all of which are hereby expressly incorporated by reference into the present application.

TECHNICAL FIELD

The present invention relates to a brain activity analyzing apparatus, a brain activity analyzing method and a biomarker apparatus, utilizing functional brain imaging.

BACKGROUND ART (Biomarker)

When biological information is converted into a numerical value and quantified as an index for quantitatively comprehending biological changes in a living body, it is called a "biomarker."

According to FDA (United States Food and Drug Administration), a biomarker is regarded as "a characteristic that is objectively measured and evaluated as an indicator of normal biological processes, pathogenic processes or pharmacological responses to a therapeutic intervention." Biomarkers representative of state of disease, changes or degree of healing are used as surrogate markers (substitute markers) to monitor efficacy in clinical tests of new drugs. Blood sugar level and cholesterol level are representative biomarkers used as indexes of lifestyle diseases. Biomarkers include not only substances of biological origin contained in urine or blood but also electrocardiogram, blood pressure, PET images, bone density, lung function and the like. Developments in genomic analysis and proteome analysis have lead to discovery of various biomarkers related to DNA, RNA or biological protein.

Biomarkers are promising for measuring therapeutic efficacy after the onset of a disease and, in addition, as routine preventive indexes, promising for disease prevention. Further, application of biomarkers to individualized medicine for selecting effective treatment avoiding side effects is expected.

In the field of neurological/mental disorder, however, though studies directed to molecular markers and the like usable as objective indexes from a biochemical or molecular genetics viewpoint have been made, it will be justified to say that they are still under consideration.

Meanwhile, a disease determination system using NIRS (Near-InfraRed Spectroscopy), classifying mental disorders such as schizophrenia and depression based on features of hemoglobin signals measured by biological optical measurement, is reported (Non-Patent Literature 1).

(Real Time Neurofeedback)

Conventionally, as therapies for Obsessive-Compulsive Disorder (OCD) as one type of neurotic disease, for example, pharmacological and behavioral treatments have been known. The pharmacological treatment uses, for example, serotonin-selective reuptake inhibitor. As the behavioral treatment, exposure response prevention therapy, combining exposure therapy and response prevention has been known.

Meanwhile, real time neurofeedback is studied as a possible therapy for neurological/mental disorder.

Functional brain imaging, including functional Magnetic Resonance Imaging (fMRI), which visualizes hemodynamic reaction related to human brain activities using Magnetic Resonance Imaging (MRI), has been used to specify an active region of a brain corresponding to a component of brain function of interest, that is, to clarify functional localization of brain, by detecting difference between those in brain activities while responding to a sensory stimulus or performing a cognitive task, and those brain activities in a resting state or while performing a control task.

Recently, real time neurofeedback technique using functional brain imaging such as functional magnetic response imaging (fMRI) is reported (Non-Patent Literature 1). Real time neurofeedback technique has come to attract attention as a possible therapy of neurological disorder and mental disorder.

Neurofeedback is one type of bio-feedback, in which a subject receives feedback about his/her brain activities and thereby learns a method of managing brain activities.

By way of example, according to a report, activities of anterior cingulate cortex are measured by fMRI, the measurements are fed back to patients on real time basis as larger or smaller fire image, and the patients are instructed to make efforts to decrease the size of the fire, then improvement was attained both in real-time and long-term chronic pain of central origin (see Non-Patent Literature 2).

(Resting State fMRI)

Further, recent studies show that even when a subject is in the resting state, his/her brain works actively. Specifically, in the brain, there is a group of nerve cells that subside when the brain works actively and are excited vigorously in the resting state. Anatomically, these cells mainly exist on the medial surface where left and right cerebral hemispheres are connected such as medial aspect of the frontal lobe, posterior cingulate cortex, precuneus, posterior portion of parietal association area and middle temporal gyrus. The regions representing baseline brain activity in the resting state are named Default Mode Network (DMN) and these regions work in synchronization as one network (see Non-Patent Literature 3).

An example of difference between brain activities of a healthy individual and those of a patient of mental disease is observed in brain activities in the default mode network. The default mode network refers to portions of one's brain that exhibit more positive brain activities when a subject is in the resting state than when the subject is performing a goal-directed task. It has been reported that abnormality is observed in the default mode network of patients of mental disorder such as schizophrenia or Alzheimer's disease as compared with healthy individuals. By way of example, it is reported that in the brain of a schizophrenia patient, correlation of activities among posterior cingulate cortex, which belongs to the default mode network, and parietal lateral cortex, medial prefrontal cortex or cerebellar cortex, is decreased in the resting state.

At present, however, it is not necessarily clear how the default mode network as such relates to the cognitive function and how the correlations of functional connectivity among brain regions relates to the above-described neurofeedback.

On the other hand, changes in correlations between activities among a plurality of brain regions caused, for example, by difference in tasks are observed, so as to evaluate functional connectivity between these brain regions. Specifically, evaluation of functional connectivity in the resting state obtained by fMRI is referred to as resting-state functional connectivity MRI (rs-fcMRI), which is utilized for clinical studies directed to various neurological/mental disorders. The conventional rs-fcMRI, however, is for observing activities of global neural network such as the default mode network described above, and more detailed functional connectivity is not yet sufficiently considered.

(DecNef Method: Decoded NeuroFeedback)

On the other hand, a new type neural feedback method referred to as decoded neurofeedback (DecNef) is reported recently (see Non-Patent Literature 4).

Human sensory and esthesic systems are ever-changing in accordance with the surrounding environment. Most of the changes occur in a certain early period of human developmental stage, or the period referred to as a "critical period." Adults, however, still keep sufficient degree of plasticity of sensory and esthesic systems to adapt to significant changes in surrounding environment. By way of example, it is reported that adults subjected to a training using specific esthesic stimulus or exposed to specific esthesic stimulus have improved performance for the training task or improved sensitivity to the esthesic stimulus, and that such results of training were maintained for a few months to a few years (see Non-Patent Literature 5). Such a change is referred to as sensory learning, and it has been confirmed that such a change occurs in every sensory organ, that is, vision, audition, olfaction, gustation, and taction.

According to DecNef, a stimulus as an object of learning is not directly applied to a subject while brain activities are detected and decoded, and only the degree of approximation to a desired brain activity is fed back to the subject to enable "sensory learning."

(Nuclear Magnetic Resonance Imaging)

Nuclear Magnetic Resonance Imaging will be briefly described in the following.

Conventionally, as a method of imaging cross-sections of the brain or the whole body of a living body, nuclear magnetic resonance imaging has been used, for example, for human clinical diagnostic imaging, which method utilizes nuclear magnetic resonance with atoms in the living body, particularly with atomic nuclei of hydrogen atoms.

As compared with "X-ray CT," which is a similar method of human tomographic imaging, characteristics of nuclear magnetic resonance imaging when applied to a human body, for example, are as follows:

(1) An image density distribution reflecting distribution of hydrogen atoms and their signal relaxation time (reflecting strength of atomic bonding) are obtained. Therefore, the shadings present different nature of tissues, making it easier to observe difference in tissues;

(2) The magnetic field is not absorbed by bones. Therefore, a portion surrounded by a bone or bones (for example, inside one's skull, or spinal cord) can easily be observed; and (3) Unlike X-ray, it is not harmful to human body and, hence, it has a wide range of possible applications.

Nuclear magnetic resonance imaging described above uses magnetic property of hydrogen atomic nuclei (protons), which are most abundant in human cells and have highest magnetism. Motion in a magnetic field of spin angular momentum associated with the magnetism of hydrogen atomic nucleus is, classically, compared to precession of spin of a spinning top.

In the following, as a description of background of the present invention, the principle of magnetic resonance will be summarized using the intuitive classical model.

The direction of spin angular momentum of hydrogen atomic nucleus (direction of axis of rotation of spinning top) is random in an environment free of magnetic field. When a static magnetic field is applied, however, the momentum is aligned with the line of magnetic force.

In this state, when an oscillating magnetic field is superposed and the frequency of oscillating magnetic field is resonance frequency $f0=\gamma B0/2\pi$ ($\gamma$: substance-specific coefficient) determined by the intensity of static magnetic field, energy moves to the side of atomic nuclei because of resonance, and the direction of magnetic vector changes (precession increases). When the oscillating magnetic field is turned off in this state, the precession gradually returns to the direction in the static magnetic field with the tilt angle returning to the previous angle. By externally detecting this process by an antenna coil, an NMR signal can be obtained.

The resonance frequency f0 mentioned above of hydrogen atom is 42.6×B0 (MHz) where B0 (T) represents the intensity of the static magnetic field.

Further, in nuclear magnetic resonance imaging, using changes appearing in detected signals in accordance with changes in the blood flow, it is possible to visualize an active portion of a brain activated in response to an external stimulus. Such a nuclear magnetic resonance imaging is specifically referred to as fMRI (functional MRI).

An fMRI uses a common MRI apparatus with additional hardware and software necessary for fMRI measurement.

The change in blood flow causes change in NMR signal intensity, since oxygenated hemoglobin has magnetic property different from that of deoxygenated hemoglobin. Hemoglobin is diamagnetic when oxygenated, and it does not have any influence on relaxation time of hydrogen atoms in the surrounding water. In contrast, hemoglobin is paramagnetic when deoxygenated, and it changes surrounding magnetic field. Therefore, when the brain receives any stimulus and local blood flow increases and oxygenated hemoglobin increases, the change can be detected by the MRI signals. The stimulus to a subject may include visual stimulus, audio stimulus, or performance of a prescribed task (see, for example, Non-Patent Literature 2).

In the studies of brain functions, brain activities are measured by measuring increase in nuclear magnetic resonance signal (MRI signal) of hydrogen atoms corresponding to a phenomenon that density of deoxygenated hemoglobin in red blood cells decrease in minute vein or capillary vessel (BOLD effect).

Particularly, in studies related to human motor function, brain activities are measured by the MRI apparatus as described above while a subject or subjects are performing some physical activity.

For human subjects, non-invasive measurement of brain functions is essential. In this aspect, decoding technique enabling extraction of more detailed information from fMRI data has been developed (see, for example, Non-Patent Literature 6). Specifically, pixel-by-pixel brain activity analysis (volumetric pixel: voxel) of brain by the fMRI enables estimation of stimulus input and state of recognition from spatial patterns of brain activity. The above-described DecNef is an application of such a decoding technique to a task related to sensory learning.

CITATION LIST

Patent Literature

PTL 1: National Publication No. 2006-132313
PTL 2: Japanese Patent Laying-Open No. 2011-000184

Non Patent Literature

NPL 1: Nikolaus Weiskopf, "Real-time fMRI and its application to neurofeedback", NeuroImage 62 (2012) 682-692
NPL 2: deCharms R C, Maeda F, Glover G H et al, "Control over brain activation and pain learned by using real-time functional MRI", Proc Natl Acad Sci USA 102(51), 18626-18631, 2005
NPL 3: Raichle M E, Macleod A M, Snyder A Z, et al. "A default mode of brain function", Proc Natl Acad Sci USA 98(2), 676-682, 2001
NPL 4: Kazuhisa Shibata, Takeo Watanabe, Yuka Sasaki, Mitsuo Kawato, "Perceptual Learning Incepted by Decoded fMRI Neurofeedback Without Stimulus Presentation", SCIENCE VOL 334 9 Dec. 2011
NPL 5: T. Watanabe, J. E. Nanez Sr, S. Koyama, I. Mukai, J. Liederman and Y. Sasaki: Greater plasticity in lower-level than higher-level visual motion processing in a passive perceptual learning task. Nature Neuroscience, 5, 1003-1009, 2002.
NPL 6: Kamitani Y, Tong F. Decoding the visual and subjective contents of the human brain. Nat Neurosci. 2005; 8: 679-85.

SUMMARY OF INVENTION

Technical Problem

As described above, it is noted that some of the brain activity analyses using functional brain imaging such as functional magnetic resonance imaging, and neurofeedback techniques using the same, are applicable to treatment of neurological/mental disorder. These methods and techniques, however, are not yet close to practical use.

When we consider application to treatment of neurological/mental disorder, brain activity analysis by functional brain imaging as the above-described biomarker is promising as non-invasive functional marker, and applications to development of diagnostic method and to searching/identification of target molecule for drug discovery for realizing basic remedy are also expected.

By way of example, consider mental disorder such as autism. Practical biomarker using genes is not yet established and, therefore, development of therapeutic agents remains difficult, since it is difficult to determine effect of medication.

Meanwhile, it has been suggested that diagnostic result of neurological disorder is predicable to some extent based on connections among brain regions derived from fMRI data of the resting state. To verify the prediction performance, however, these studies use only brain functions measured in one facility and, hence, usability as a biomarker has not yet been sufficiently verified.

Therefore, conventionally, it has been unclear how to configure a biomarker utilizing above-described functional brain imaging.

The present invention was made to solve such a problem, and its object is to provide a brain activity analyzing apparatus and a brain activity analyzing method that can provide data enabling objective determination as to whether the state of brain activity is healthy or having a disease.

Another object of the present invention is to provide a brain activity analyzing apparatus and a brain activity analyzing method for realizing a discrimination process using functional brain imaging to support diagnosis of neurological/mental disorder.

A further object of the present invention is to provide a brain activity analyzing apparatus, a brain activity analyzing method, and a biomarker apparatus, for realizing a biomarker utilizing functional brain imaging.

Solution to Problem

According to an aspect, the present invention provides a brain activity analyzing apparatus, including: a discriminator generating means for generating a discriminator from signals measured time-sequentially in advance by a brain activity detecting apparatus detecting signals indicative of brain activities at a plurality of prescribed regions in a brain of a plurality of subjects, the discriminator generating means extracting at least a contraction expression common to attributes of the plurality of subjects, from among correlations of brain activities at the plurality of prescribed regions, and generating a discriminator related to a specific attribute of the attributes of subjects with respect to the extracted contraction expression; the brain activity analyzing apparatus further including: a storage device storing information for specifying the discriminator: and discriminating means for performing a discriminant process on input data based on the discriminator specified by the information stored in the storage device.

Preferably, the specific attribute is a disease discriminant label.

Preferably, the attributes of subjects include a label of a medicine administered to the subjects.

Preferably, the brain activity detecting apparatus includes a plurality of brain activity measuring devices; and the discriminator generating means includes extracting means for extracting the contraction expression common in attributes of the plurality of subjects and conditions for measurement of the plurality of brain activity measuring devices, by variable selection from correlations of brain activities at the plurality of prescribed regions.

Preferably, the discriminator generating means includes regression means for generating the discriminator by regression of performing further variable selection on the extracted contraction expression.

Preferably, the extracting means includes correlation analyzing means for calculating a correlation matrix of activities at the plurality of prescribed regions from the signals detected by the brain activity detecting device, and for extracting the contracted expression by executing regularized canonical correlation analysis between attributes of the subjects and non-diagonal elements of the correlation matrix.

Preferably, the regression means includes regression analysis means for generating a discriminator by sparse logistic regression on a result of the regularized canonical correlation analysis and the attributes of the subjects.

Preferably, the plurality of brain activity measuring devices are devices for measuring brain activities in a time-series by functional brain imaging installed at a plurality of different locations, respectively.

Preferably, the discriminant process is discrimination of a disease label indicating whether the subject is healthy or a patient of a neurological/mental disorder.

Preferably, the attributes of the subjects include a disease label indicating whether the subject is healthy or a patient of a neurological/mental disorder, a label indicating individual nature of the subject, and information characterizing measurement by the brain activity detecting device; and the discriminant process is discrimination of a disease label indicating whether the subject is healthy or a patient of a neurological/mental disorder.

Preferably, the regularized canonical correlation analysis is a canonical correlation analysis with L1 regularization.

Preferably, the brain activity measuring device picks up a resting-state functional connectivity magnetic resonance image.

According to another aspect, the present invention provides a brain activity analyzing method for a computer including a processing device and a storage device to analyze brain activities, including the step of: generating a discriminator from signals measured in a time-series in advance by a brain activity detecting apparatus detecting signals indicative of brain activities at a plurality of prescribed regions in a brain of a plurality of subjects: wherein the step of generating the discriminator includes the step of extracting at least a contraction expression common to attributes of the plurality of subjects, from among correlations of brain activities at the plurality of prescribed regions, and generating a discriminator related to a specific attribute of the attributes of subjects with respect to the extracted contraction expression; the method further including the steps of: storing information for specifying the discriminator in the storage device; and performing a discriminant process on input data based on the discriminator specified by the information stored in the storage device.

Preferably, the specific attribute is a disease discriminant label.

Preferably, the attributes of subjects include a label of a medicine administered to the subjects.

Preferably, the brain activity detecting apparatus includes a plurality of brain activity measuring devices; and the discriminator generating step includes the step of extracting the contraction expression common in attributes of the plurality of subjects and conditions for measurement of the plurality of brain activity measuring devices, by variable selection from correlations of brain activities at the plurality of prescribed regions.

Preferably, the discriminator generating step includes the step of generating the discriminator by regression of performing further variable selection on the extracted contraction expression.

According to a still further aspect, the present invention provides a biomarker apparatus for generating an output as a biomarker by computer analysis of brain activities, including a storage device for storing information for specifying a discriminator; wherein the discriminator is calculated from signals measured in a time-series in advance by a brain activity detecting apparatus detecting signals indicative of brain activities at a plurality of prescribed regions in a brain of a plurality of subjects, by extracting at least a contraction expression common to attributes of the plurality of subjects, from among correlations of brain activities at the plurality of prescribed regions, and generated for a disease discrimination label of the attributes of subjects with respect to the extracted contraction expression; the apparatus further including a processing device configured to perform a discriminant process on input data based on the discriminator specified by the information stored in the storage device.

Preferably, the attributes of subjects include a label of a medicine administered to the subjects.

Advantageous Effects of Invention

By the present invention, it becomes possible to realize a brain activity analyzing apparatus and a brain activity analyzing method that can provide data enabling objective determination as to whether the state of brain activity is healthy or having a disease.

Further, by the present invention, it becomes possible to realize a biomarker utilizing functional brain imaging, for neurological/mental disorder.

BRIEF DESCRIPTION OF DRAWINGS

FIG. 12 shows properties of the biomarker.

DESCRIPTION OF EMBODIMENTS

Figure 1:
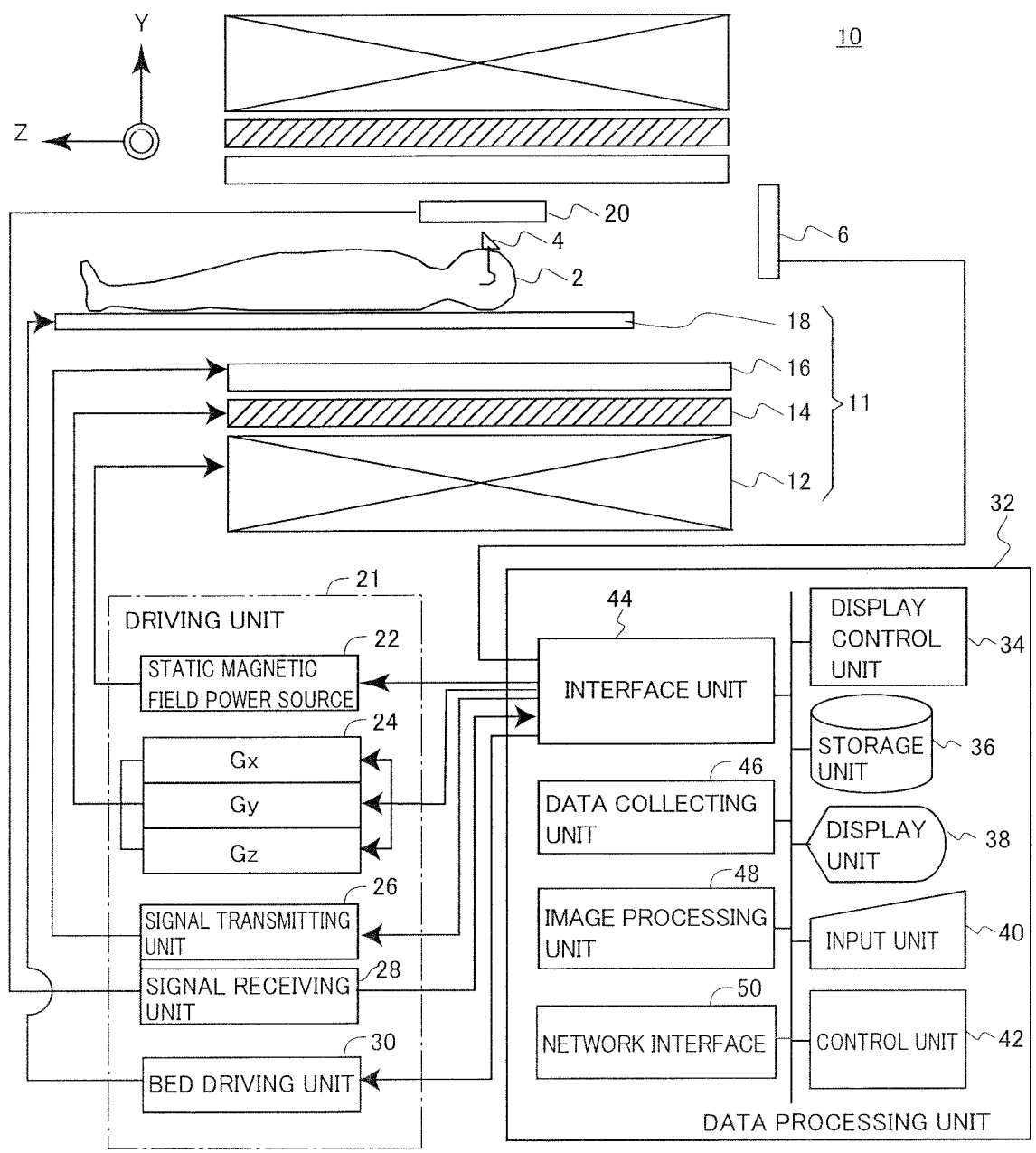
FIG. 1 is a schematic diagram showing an overall configuration of an MRI apparatus 10.

In the following, a configuration of an MRI system in accordance with embodiments of the present invention will be described with reference to the drawings. In the embodiments below, components or process steps denoted by the same reference characters are the same or corresponding components or steps and, therefore, description thereof will not be repeated unless necessary.

First Embodiment

FIG. 1 is a schematic diagram showing an overall configuration of an MRI apparatus 10.

Referring to FIG. 1, MRI apparatus 10 includes: a magnetic field applying mechanism 11 applying a controlled magnetic field to, and irradiating with RF wave, a region of interest of a subject 2; a receiving coil 20 receiving a response wave (NMR signal) from subject 2 and outputting an analog signal; a driving unit 21 controlling the magnetic field applied to subject 2 and controlling transmission/reception of RF wave: and a data processing unit 32 configuring a control sequence of driving unit 21 and processing various data signals to generate an image.

Here, a central axis of a cylindrical bore in which subject 2 is placed is regarded as a Z-axis, and a horizontal direction orthogonal to the Z-axis and the vertical direction orthogonal to the Z-axis are defined as X-axis and Y-axis, respectively.

In MRI apparatus 10 having such a configuration, because of the static magnetic field applied by magnetic field applying mechanism 11, nuclear spins of atomic nuclei forming subject 2 are oriented in the direction of magnetic field (Z-axis) and perform precession with the direction of magnetic field being an axis, with Larmor frequency unique to the atomic nuclei.

When irradiated with an RF pulse of the same Larmor frequency, the atoms resonate, absorb energy and are excited, resulting in nuclear magnetic resonance (NMR). When the irradiation with RF pulse is stopped after the resonance, the atoms discharge energy and return to the original, steady state. This process is referred to as a relaxation process. In the relaxation process, the atoms output electromagnetic wave (NMR signal) having the same frequency as the Larmor frequency.

The output NMR signal is received by receiving coil 20 as a response wave from subject 2, and the region of interest of subject 2 is imaged by data processing unit 32.

Magnetic field applying mechanism 11 includes a static magnetic field generating coil 12, a magnetic field gradient generating coil 14, an RF irradiating unit 16, and a bed 18 for placing subject 2 in the bore.

By way of example, subject 2 lies on his/her back on bed 18. Though not limited, subject 2 may view an image displayed on a display 6 mounted vertical to the Z-axis, using prism glasses 4. Visual stimulus is applied to subject 2 by an image on display 6. In another embodiment, visual stimulus to subject 2 may be applied by projecting an image in front of subject 2 using a projector.

Such a visual stimulus corresponds to presentation of feedback information in the above-described neurofeedback.

Driving unit 21 includes a static magnetic field power source 22, a magnetic field gradient power source 24, a signal transmitting unit 26, a signal receiving unit 28, and a bed driving unit 30 for moving bed 18 to any position along the Z-axis.

Data processing unit 32 includes: an input unit 40 for receiving various operations and information input from an operator (not shown); a display unit 38 for displaying various images and various pieces of information related to the region of interest of subject 2, on a screen; a display control unit 34 for controlling display of display unit 38: a storage unit 36 for storing programs to cause execution of various processes, control parameters, image data (structural images and the like) and other electronic data; a control unit 42 controlling operations of various functional units, including generating a control sequence for driving the driving unit 21; an interface unit 44 for executing transmission/reception of various signals to/from driving unit 21; a data collecting unit 46 for collecting data consisting of a group of NMR signals derived from the regions of interest; an image processing unit 48 for forming an image based on the data of NMR signals; and a network interface 50 for executing communication with a network.

Data processing unit 32 may be a dedicated computer, or it may be a general purpose computer executing functions of causing operations of various functional units, in which designated operations, data processing and generation of control sequence are realized by a program or programs stored in storage unit 36. In the following, description will be given assuming that data processing unit 32 is implemented by a general purpose computer.

Static magnetic field generating coil 12 causes a current supplied from a static magnetic field power source 22 to flow through a helical coil wound around the Z-axis to generate an induction magnetic field, and thereby generates a static magnetic field in the Z-direction in the bore. The region of interest of subject 2 is placed in the region of highly uniform static magnetic field formed in the bore. More specifically, here, static magnetic field generating coil 12 is comprised of four air core coils, forms a uniform magnetic field inside by the combination of the coils, and attains orientation of the spins of prescribed atomic nuclei in the body of subject 2, or more specifically, the spins of hydrogen atomic nuclei.

Magnetic field gradient generating coil 14 is formed of X-, Y- and Z-coils (not shown), and provided on an inner peripheral surface of cylindrical static magnetic field generating coil 12.

These X-, Y- and Z-coils superpose magnetic field gradients on the uniform magnetic field in the bore with the X-axis, Y-axis and Z-axis directions switched in turn, whereby creating intensity gradient in the static magnetic field. When excited, the Z-coil tilts the magnetic field intensity to the Z-direction and thereby defines a resonance surface; the Y-coil applies a tilt for a short period of time immediately after application of the magnetic field in the Z-direction, and thereby adds phase modulation in proportion to the Y-coordinate, to the detected signal (phase encoding); and thereafter the X-coil applies a tilt when data is collected, and thereby adds frequency modulation in proportion to the X-coordinate, to the detected signal (frequency encoding).

The switching of superposed magnetic field gradients is realized as different pulse signals are output to the X-, Y- and Z-coils from the magnetic field gradient power source 24 in accordance with a control sequence. Thus, the position of subject 2 expressed by the NMR can be specified, and positional information in three-dimensional coordinates necessary for forming an image of subject 2 are provided.

Here, using the orthogonally crossing three sets of magnetic field gradients, allocating slice direction, phase encoding direction and frequency encoding direction to the magnetic fields respectively and by combining these, images can be taken from various angles. By way of example, in addition to transverse slice in the same direction as taken by an X-ray CT apparatus, saggital and coronal slices orthogonal thereto, as well as an oblique slice, of which direction vertical to its plane is not parallel to any of the axes of three orthogonally crossing magnetic field gradients, can be imaged.

RF irradiating unit 16 irradiates a region of interest of subject 2 with RF (Radio Frequency) pulses based on a high-frequency signal transmitted from a signal transmitting unit 26 in accordance with a control sequence.

Though RF irradiating unit 16 is built in magnetic field applying mechanism 11 in FIG. 1, it may be mounted on bed 18 or integrated with receiving coil 20.

Receiving coil 20 detects a response wave (NMR signal) from subject 2, and in order to detect the NMR signal with high sensitivity, it is arranged close to subject 2.

Here, when an electromagnetic wave of NMR signal crosses a coil strand of receiving coil 20, a weak current is generated by electromagnetic induction. The weak current is amplified by signal receiving unit 28 and converted from an analog signal to a digital signal, and then transmitted to data processing unit 32.

The mechanism here is as follows. To a subject 2 in a state of static magnetic field with Z-axis magnetic field gradient added, a high-frequency electromagnetic field of resonance frequency is applied through RF irradiating unit 16. Prescribed atomic nuclei at a portion where magnetic field intensity satisfies the condition of resonance, for example, hydrogen atomic nuclei, are selectively excited and start resonating. Prescribed atomic nuclei at a portion satisfying the condition of resonance (for example, a slice of prescribed thickness of subject 2) are excited, and spin axes of atomic nuclei concurrently start precession. When the excitation pulse is stopped, electromagnetic waves irradiated by the atomic nuclei in precession induce a signal in receiving coil 20 and, for some time, this signal is continuously detected. By this signal, a tissue containing the prescribed atoms in the body of subject 2 is monitored. In order to know the position where the signal comes from, X- and Y-magnetic field gradients are added and the signal is detected.

Based on the data built in storage unit 36, image processing unit 48 measures detected signals while repeatedly applying excitation signals, reduces resonance frequency to X-coordinate by a first Fourier transform, restores Y-coordinate by a second Fourier transform, and thus, displays a corresponding image on display unit 38.

For example, by picking-up the above-described BOLD signal on real-time basis using the MRI system as described above and performing an analysis, which will be described later, on the time-sequentially picked-up images by control unit 42, it is possible to take resting-state functional connectivity MRI (rs-fcMRI).

Figure 2:
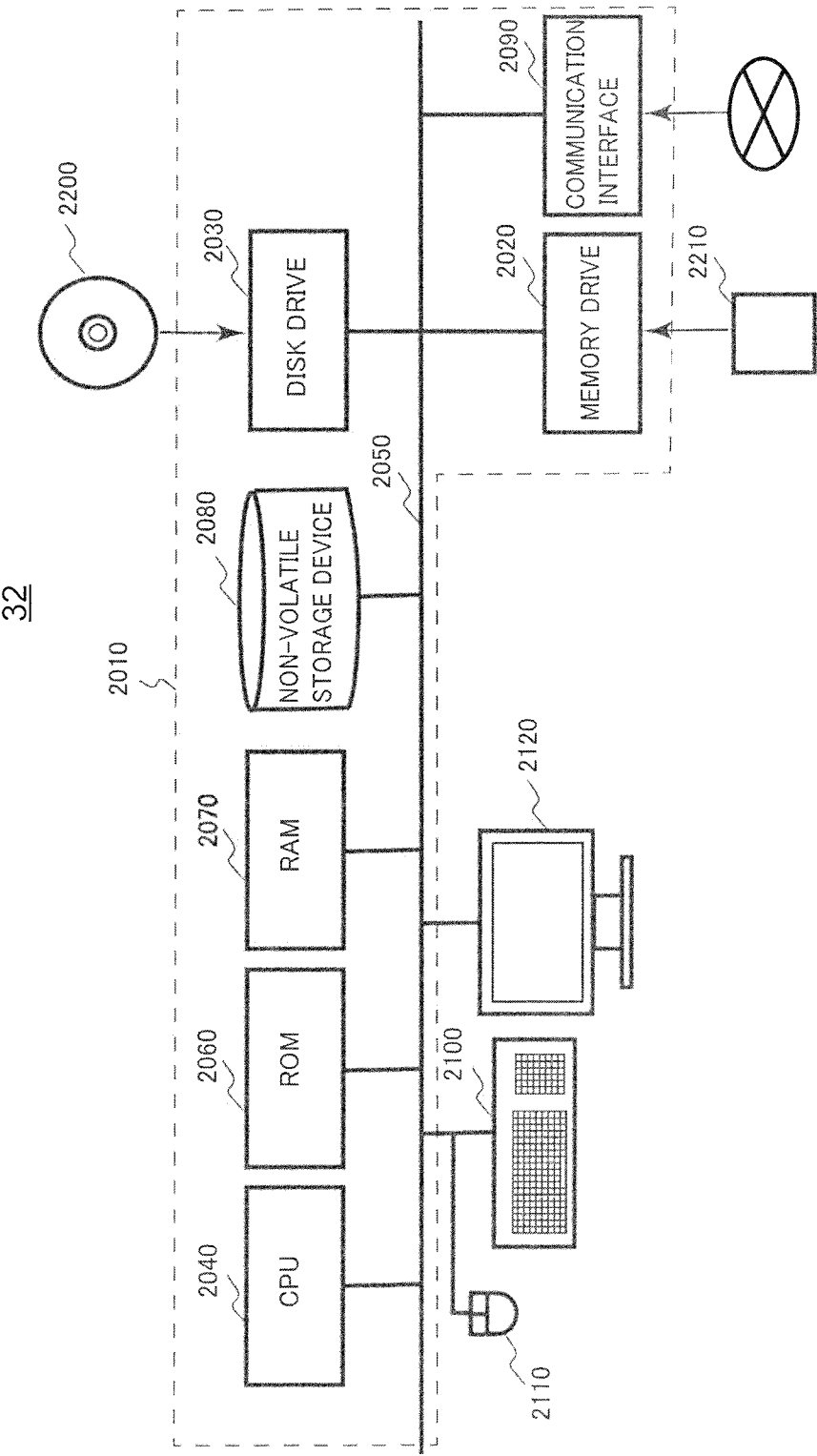
FIG. 2 is a hardware block diagram of data processing unit 32.

FIG. 2 is a hardware block diagram of data processing unit 32.

Though the hardware of data processing unit 32 is not specifically limited as described above, a general-purpose computer may be used.

Referring to FIG. 2, a computer main body 2010 of data processing unit 32 includes, in addition to a memory drive 2020 and a disk drive 2030, a CPU 2040, a bus 2050 connected to disk drive 2030 and memory drive 2020, an ROM 2060 for storing programs such as a boot-up program, an RAM 2070 for temporarily storing instructions of an application program and providing a temporary memory space, a non-volatile storage device 2080 for storing an application program, a system program and data, and a communication interface 2090. Communication interface 2090 corresponds to an interface unit 44 for transmitting/receiving signals to/from driving unit 21 and the like and a network interface 50 for communicating with another computer through a network, not shown. As non-volatile storage device 2080, a hard disk (HDD), a solid state drive (SSD) or the like may be used.

By operation processes executed by CPU 2040 in accordance with a program, various functions of data processing unit 32 including functions of control unit 42, data collecting unit 46 and image processing unit 48 are realized.

A program or programs causing data processing unit 32 to execute the function of the present embodiment as described above may be stored in a CD-ROM 2200 or a memory medium 2210 and inserted to disk drive 2030 or memory drive 2020 and may further by transferred to non-volatile storage device 2080. The program is loaded to RAM 2070 before execution.

Data processing unit 32 further includes a keyboard 2100 and a mouse 2110 as input devices, and a display 2120 as an output device. Keyboard 2100 and mouse 2110 correspond to input unit 40 and display 2120 corresponds to display unit 38.

The program realizing the function of data processing unit 32 as described above may not necessarily include an operating system (OS) for executing the function of information processing apparatus such as computer main body 2010. The program may only include those portions of instructions which can call appropriate functions (modules) in a controlled manner to attain a desired result. The manner how data processing unit 32 operates is well known and, therefore, detailed description will not be given here.

It is noted that one or a plurality of computers may be used to execute the program described above. In other words, either centralized or distributed processing may be possible.

Figure 3:
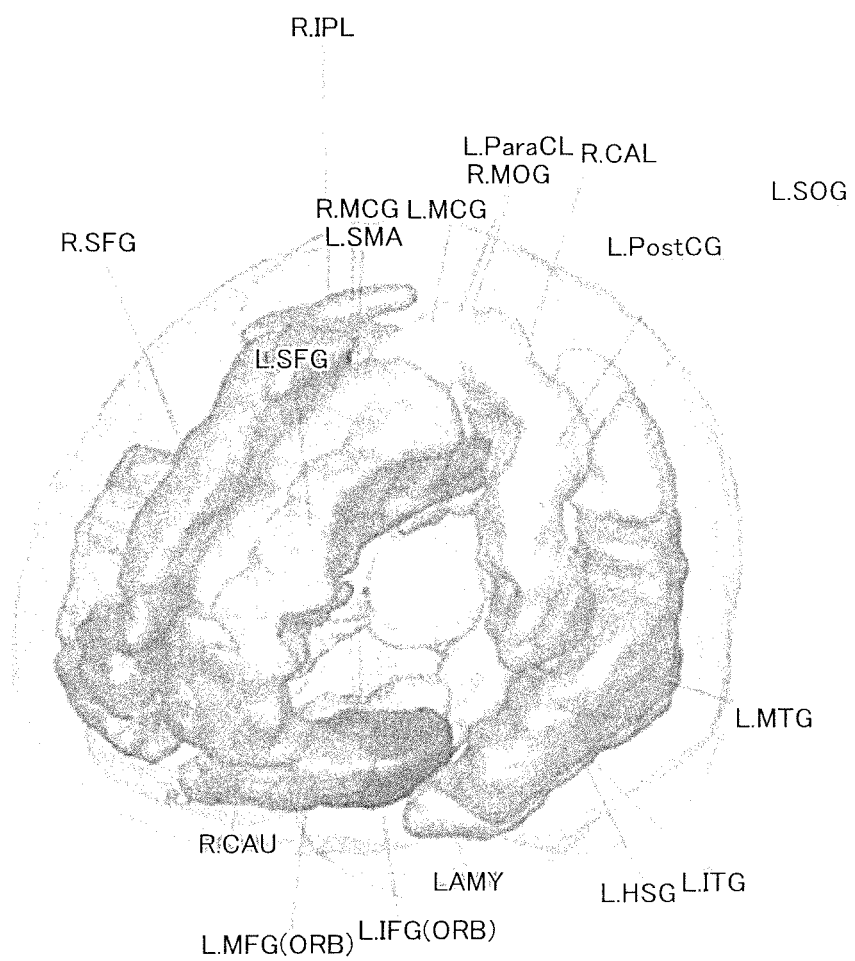
FIG. 3 shows regions of interest (ROI) of a brain imaged by rs-fcMRI in accordance with an embodiment.

FIG. 3 shows regions of interest (ROI) of a brain imaged by rs-fcMRI in accordance with an embodiment.

Here, a biomarker related to Autistic Spectrum Disorder (ASD) will be described as an example, and ninety-three regions are used as regions of interest.

Such regions of interest include, by way of example, the following:

Dorsomedial Prefrontal Cortex (DMPFC);
Ventromedial Prefrontal Cortex (VMPFC);
Anterior Cingulate Cortex (ACC);
Cerebellar Vermis;
Left Thalamus;
Right Inferior Parietal Lobe;
Right Caudate Nucleus;
Right Middle Occipital Lobe; and
Right Middle Cingulate Cortex.

It is noted, however, that the brain regions used may not be limited to those above.

For instance, the regions to be selected may be changed in accordance with the neurological/mental disorder to be studied.

Figure 4:
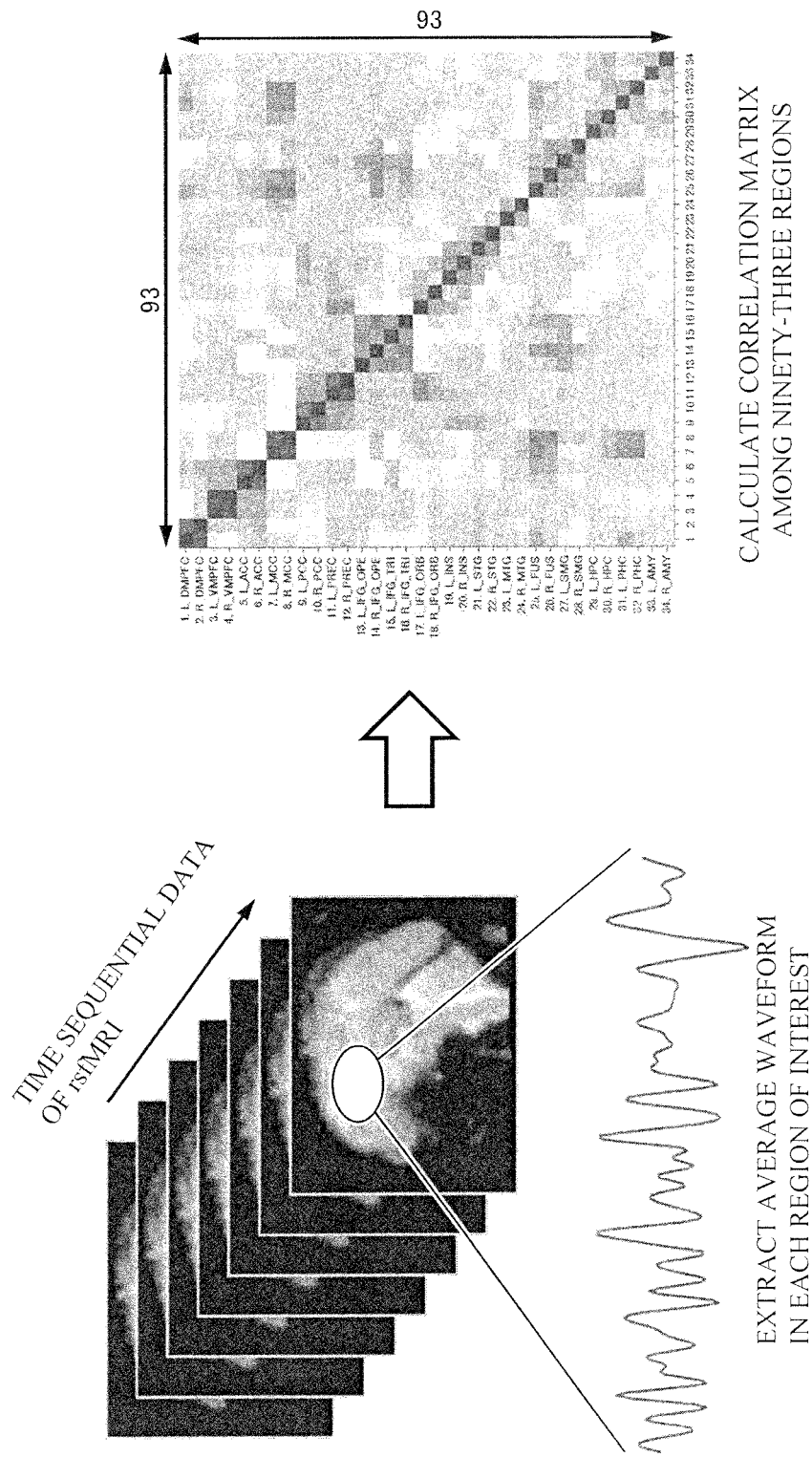
FIG. 4 shows a concept of a procedure for extracting correlation matrix representing correlations of functional connectivity in the resting state.

FIG. 4 shows a concept of a procedure for extracting correlation matrix representing correlations of functional connectivity in the resting state, from the regions of interest such as shown in FIG. 3.

Referring to FIG. 4, from fMRI data of n (n: natural number) time points in the resting state measured on real-time basis, average "degree of activity" of each region of interest is calculated, and correlations among the brain regions (among the regions of interest) are calculated.

Here, ninety-three regions are picked up as regions of interest and, therefore, the number of independent non-diagonal elements in the correlation matrix will be, considering the symmetry, $$(93 \times 93 - 93)/2 = 4278.$$

In FIG. 4, only the correlations of 34×34 are shown.

Figure 5:
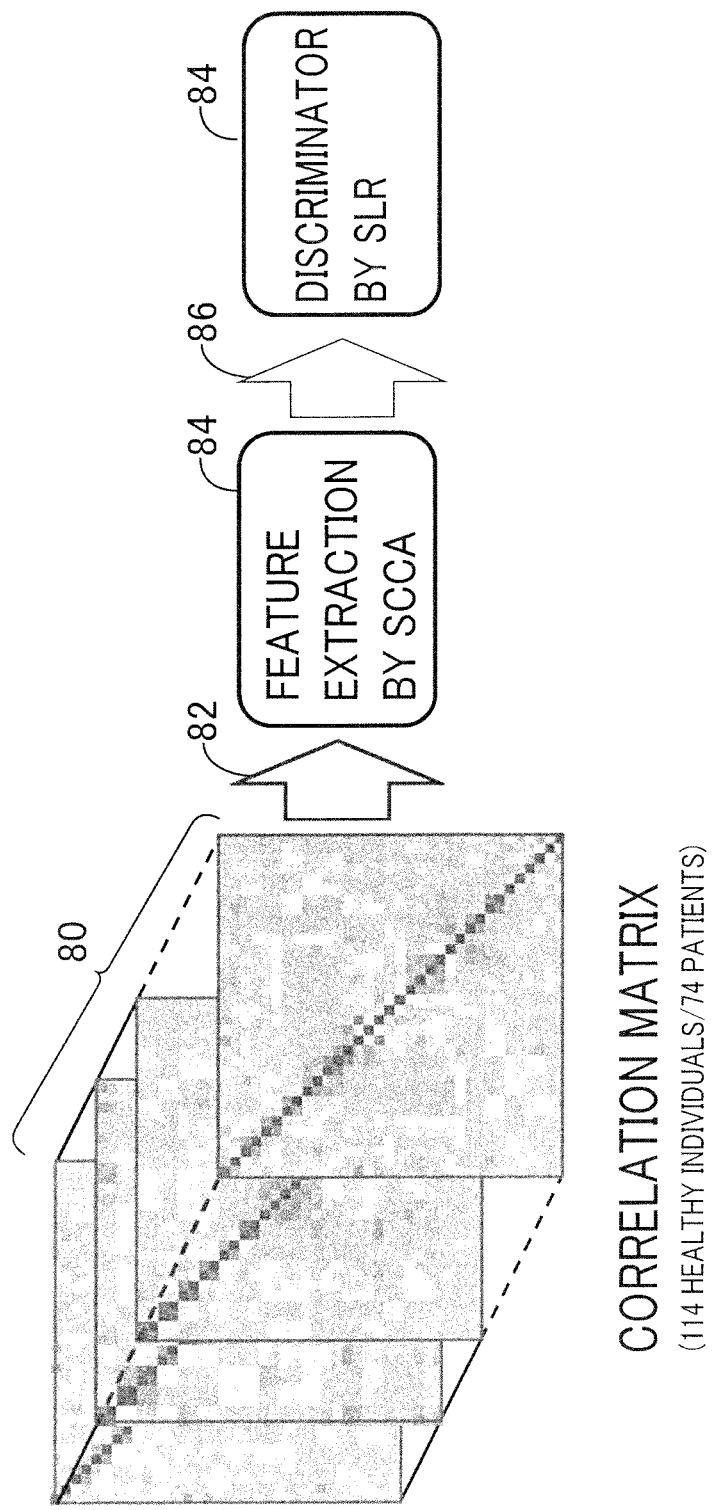
FIG. 5 shows a concept of a process for generating a discriminator serving as a biomarker, from the correlation matrix.

FIG. 5 shows a concept of a process for generating a discriminator serving as a biomarker, from the correlation matrix described with reference to FIG. 4.

Referring to FIG. 5, from data of resting-state functional connectivity MRI obtained by measuring a group of healthy subjects (in this example, 114 individuals) and a group of patients (in this example, seventy-four individuals), data processing unit 32 derives correlation matrix 80 of degree of activity among brain regions (regions of interest) in accordance with a procedure that will be described later.

Thereafter, by data processing unit 32, feature extraction 84 is performed by regularized canonical correlation analysis 82 on the correlation matrix and on the attributes of subjects including disease/healthy labels of the subjects. Here, "regularization" generally refers to a method of preventing over-learning by adding a regularization term to an error function in machine learning and statistics and thereby restricting complexity/degree of freedom of a model. If the result of regularized canonical correlation analysis results in sparse explanatory variables this process will be specifically referred to as sparse canonical correlation analysis (SCCA). In the following, an example employing SCCA will be described.

Further, by data processing unit 32, based on the result of regularized canonical correlation analysis, a discriminator 88 is generated from discriminant analysis 86 by sparse logistic regression.

As will be described later, the data of healthy group and the patient group are not limited to those measured by the MRI itself. Data measured by a different MRI apparatus may also be integrated, to generate the discriminator. Generally speaking, data processing unit 32 may not necessarily be a computer for executing control of the MRI apparatus, and it may be a computer specialized in generating the discriminator by receiving measurements data from a plurality of MRI apparatuses and performing the discriminant process by using the generated discriminator.

Figure 6:
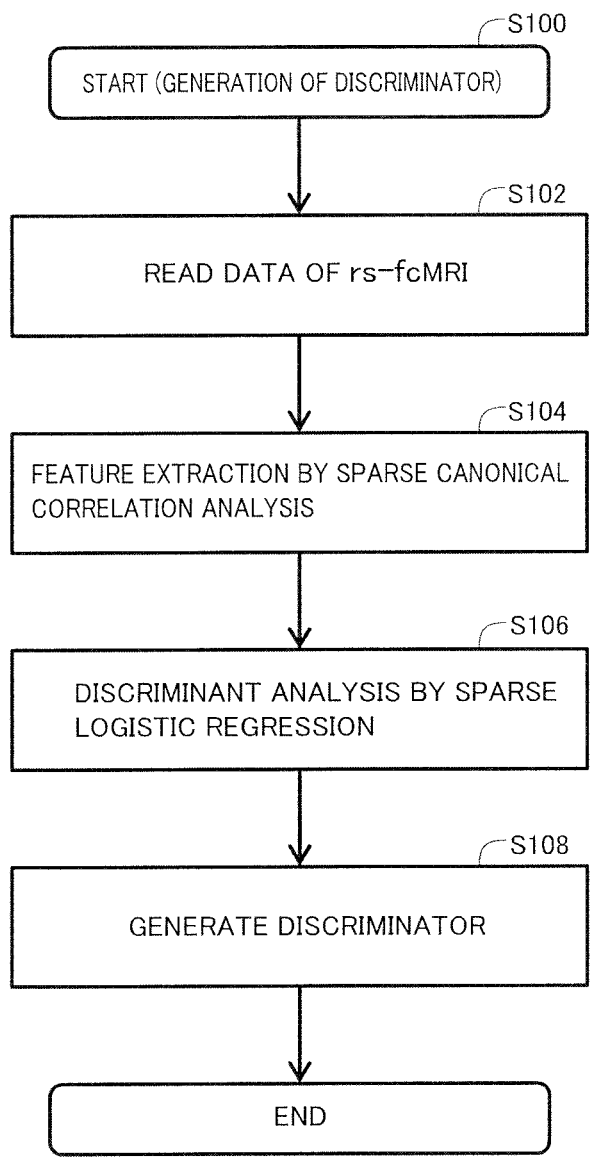
FIG. 6 is a flowchart representing a process executed by data processing unit 32 for generating the discriminator serving as the biomarker.

FIG. 6 is a flowchart representing a process executed by data processing unit 32 for generating the discriminator serving as the biomarker.

In the following, the process described with reference to FIG. 5 will be discussed in greater detail with reference to FIG. 6.

The biggest problem posed when a biomarker is to be generated based on the discriminant label of a disease of a subject and connections of brain regions derived from the fMRI data in the resting state is that the number of data dimensions is overwhelmingly larger than the number of data. Therefore, if training of a discriminator for predicting the disease discriminant label (here, the label indicating whether the subject has the disease or healthy will be referred to as the "disease discriminant label") is done using a data set without regularization, the discriminator will be over-fitted, and the prediction performance for unknown data significantly decreases.

Generally, in machine learning, a process to enable explanation of observed data with a smaller number of explanatory variables is referred to as "variable selection (or feature extraction)." In the present embodiment, "extraction of contraction expression" refers to variable selection (feature extraction) to enable formation of the discriminator with smaller number of correlation values in the machine learning of the discriminator for predicting the discriminant label of a disease to be studied from among "a plurality of correlation values (a plurality of connections) of the degree of activity among brain regions (regions of interest)," that is, to select correlation values of higher importance as the explanatory variables.

In the present embodiment, as the method of feature extraction, regularization is adopted. In this manner, canonical correlation analysis is performed with regularization and obtaining sparse variables, so as to leave explanatory variables of higher importance. This process is referred to as sparse canonical correlation analysis. More specifically, as the method of regularization also results in sparse variables, we can use a method of imposing a penalty to the magnitude of absolute value of parameters for canonical correlation analysis referred to as "L1 regularization" as will be described in the following.

Specifically, referring to FIG. 6, when the process for generating the discriminator starts (S100), data processing unit 32 reads rs-fcMRI data of each subject from storage unit 36 (S102), and performs feature extraction by SCCA (S104).

In the following, L1 regularization canonical correlation analysis will be described. As to the L1 regularization canonical correlation analysis, see, for example, the reference below.

Reference: Witten D M, Tibshirani R, and T Hastie. A penalized matrix decomposition, with applications to sparse principal components and canonical correlation analysis. Biostatistics, Vol. 10, No. 3, pp. 515-534, 2009.

First, in general Canonical Correlation Analysis (CCA), a data pair $x_1$ and $x_2$ as given below is considered. It is noted that the variables $x_1$ and $x_2$ are standardized to have an average zero and standard deviation one. Further, it is assumed that each of the data pair $x_1$ and $x_2$ has the data number of n.

$x_1 \in R^{n \times p_1}$, $x_2 \in R^{n \times p_2}$

Here, according to CCA, parameters $w_1 \in R^{p_1}$, $w_2 \in R^{p_2}$ that can maximize the correlation between $z_1 = x_1 w_1$, $z_2 = x_2 w_2$ are calculated. That is, the following optimization problem is solved.

Under the condition of $$w_1^T x_1^T x_1 w_1 = w_2^T x_2^T x_2 w_2 = 1$$

$$\max_{w_1, w_2} w_1^T x_1^T x_2 w_2.$$

In contrast, by introducing L1 regularization, the process will be to solve the following optimization problem.

Under the condition of $$\|w_1\|^2 \leq 1, \|w_2\|^2 \leq 1, \|w_1\|_1 \leq c_1, \|w_2\|_1 \leq c_2,$$

$$\max_{w_1, w_2} w_1^T x_1^T x_2 w_2$$

Here, $c_1$ and $c_2$ are parameters representing the strength of L1 regularization, and they are set appropriately in accordance with the data by various known methods. The suffix "1"' on the lower right side of $\|w_1\|_1$ and $\|w_2\|_1$ represents that $\|w_1\|$ and $\|w_2\|$ are L1 norms.

As the constraint condition for L1 regularization is added, the values of those elements of lower importance of the elements of parameters $w_1$ and $w_2$ will become zero and, hence, the features (explanatory variables) become sparse.

Thereafter, data processing unit 32 performs discriminant analysis by SLR based on the result of SCCA (S106).

SLR refers to a method of logistic regression analysis expanded to a frame of Bayes estimation, in which dimensional compression of a feature vector is performed concurrently with weight estimation for discriminant. This is useful when the feature vector of data has a very large number of dimensions and includes many unnecessary feature elements. For unnecessary feature elements, weight parameter in linear discriminant analysis will be set to zero (that is, variable selection is done), so that only a limited number of feature elements related to the discriminant are extracted (sparseness).

In SLR, probability p of obtained feature data belonging to a class is calculated class by class, and the feature data is classified to the class corresponding to the highest output value p. The value p is output by a logistic regression equation. Weight estimation is done by ARD (Automatic Relevance Determination), and feature element less contributing to class determination is removed from the calculation as its weight comes closer to zero.

Specifically, using the features extracted by the L1 regularization CCA as described above, the discriminator based on the hierarchical Bayes' estimation as will be described in the following estimates the disease healthy label.

Here, assuming that the features $z_1=w_1x_1$ derived from CCA are input to SLR and S={0, 1} is a label of disease (S=1)/healthy (S=0), then, the probability of the SLR output being S=1 is defined as follows.

$$p(z_1, w) = \frac{1}{1+e^{-w^T z_1}} \Lambda \qquad (1)$$

Here, the distribution of parameter vector w is set to the normal distribution as given below. In the equation, α represents a hyper parameter vector representing variance of normal distribution of vector w.

$$p(w|\alpha)=N(w|0,\text{diag}(\alpha))$$

Further, by setting the distribution of hyper parameter vector α as follows, distribution of each parameter is estimated by hierarchical Bayes' estimation.

$$p(\alpha) = \prod_j \Gamma(\alpha_j | a^0, b^0)$$

Here, Γ represents a Γ distribution, and $a^0$ and $b^0$ are parameters determining gamma distribution of hyper parameter vector α. The i-th element of vector α is represented by $\alpha_i$.

As to the SLR, see, for example, the reference below.

Reference: Okito Yamashita, Masaaki Sato, Taku Yoshioka, Frank Tong, and Yukiyasu Kamitani. "Sparse Estimation automatically selects voxels relevant for the decoding of fMRI activity patterns." NeuroImage, Vol. 42, No. 4, pp. 1414-1429, 2008.

Based on the result of discriminant analysis as described above, the discriminator that discriminates the disease/healthy label (label for discriminating the disease) on the input features is generated (S108). The information for specifying the generated discriminator (data related to the function form and parameters) is stored in storage unit 36, and, when test data is input later, will be used for the discriminant process when the discriminant label of the disease is estimated for the test data.

Specifically, based on doctors' diagnosis in advance, the subjects are divided to a group of healthy individuals and a group of patients. Correlations (connectivity) of degree of activities among brain regions (regions of interest) of the subjects will be measured. By machine learning of measurement results, the discriminator is generated to discriminate whether test data of a new subject, different from those above, fits to disease or healthy. The discriminator functions as a biomarker of mental disorder. Here, the "disease discriminant label" as the biomarker output may include a probability that the subject has the disease (or probability that the subject is healthy), since the discriminator is generated by logistic regression. By way of example, an indication "Probability of having the disease: ○○%" may be output. Such a probability may be used as a "diagnosis marker."

As to the attribute to be the output of the discriminator is not necessarily limited to discrimination of a disease, and it may be an output related to a different attribute. In that case also, a discrete determination result indicating to which class it belongs may be output, or a continuous value such as a probability of the attribute belonging to a certain class may be output.

In summary, in biomarker learning (generation), in order to generate the biomarker for mental disorder, data of resting state functional connectivity MRI (rs-fcMRI) is used as an input, feature extraction is done by L1 regularization CA as described above, and using the extracted features as the input, disease/healthy discriminant is done by the SLR.

In the foregoing, it is assumed that the features $z_1=w_1x_1$ derived from CCA are used as the features to be the input to SLR.

The features to be used as the input to SLR, however, are not limited to the above.

Figure 7:
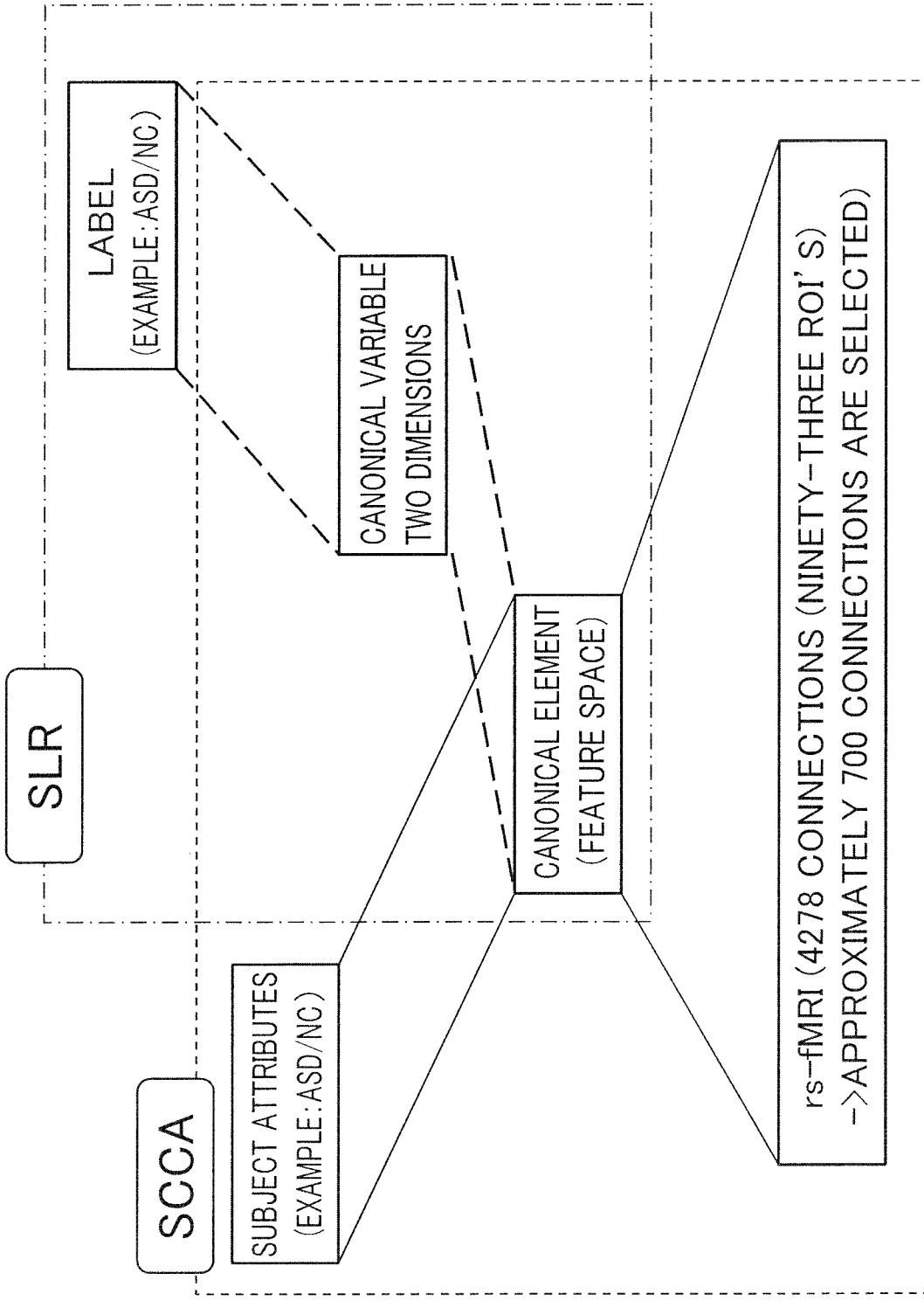
FIG. 7 shows features obtained by Sparse Canonical Correlation Analysis (SCCA) (SCCA feature space) and a concept of a procedure for generating the discriminator by and Sparce Logistic Regression (SLR) using the features as an input.
Figure 8:
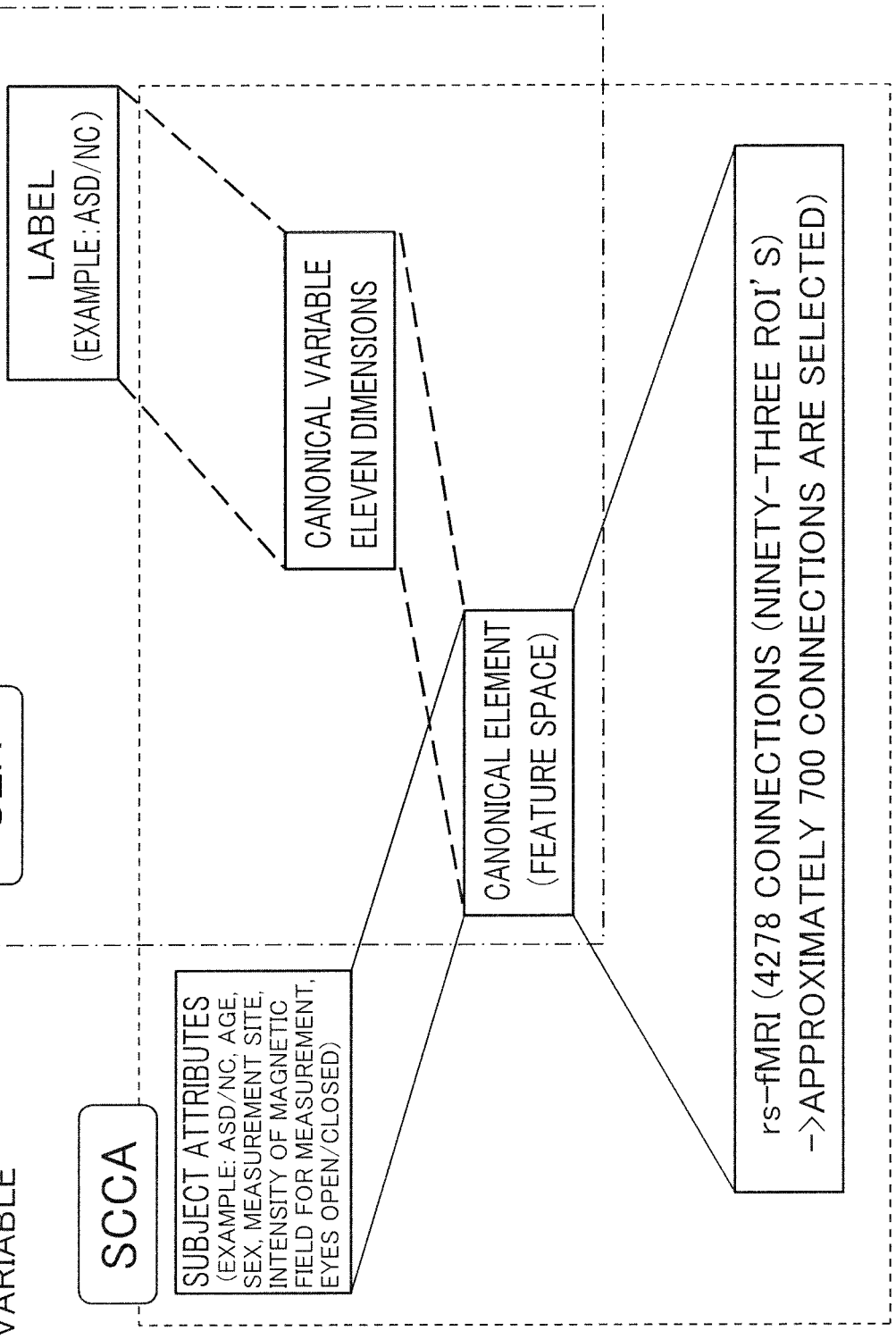
FIG. 8 shows features (SCCA feature space) obtained by SCCA and a concept of a procedure for generating the discriminator by SLR using the features as an input.
Figure 9:
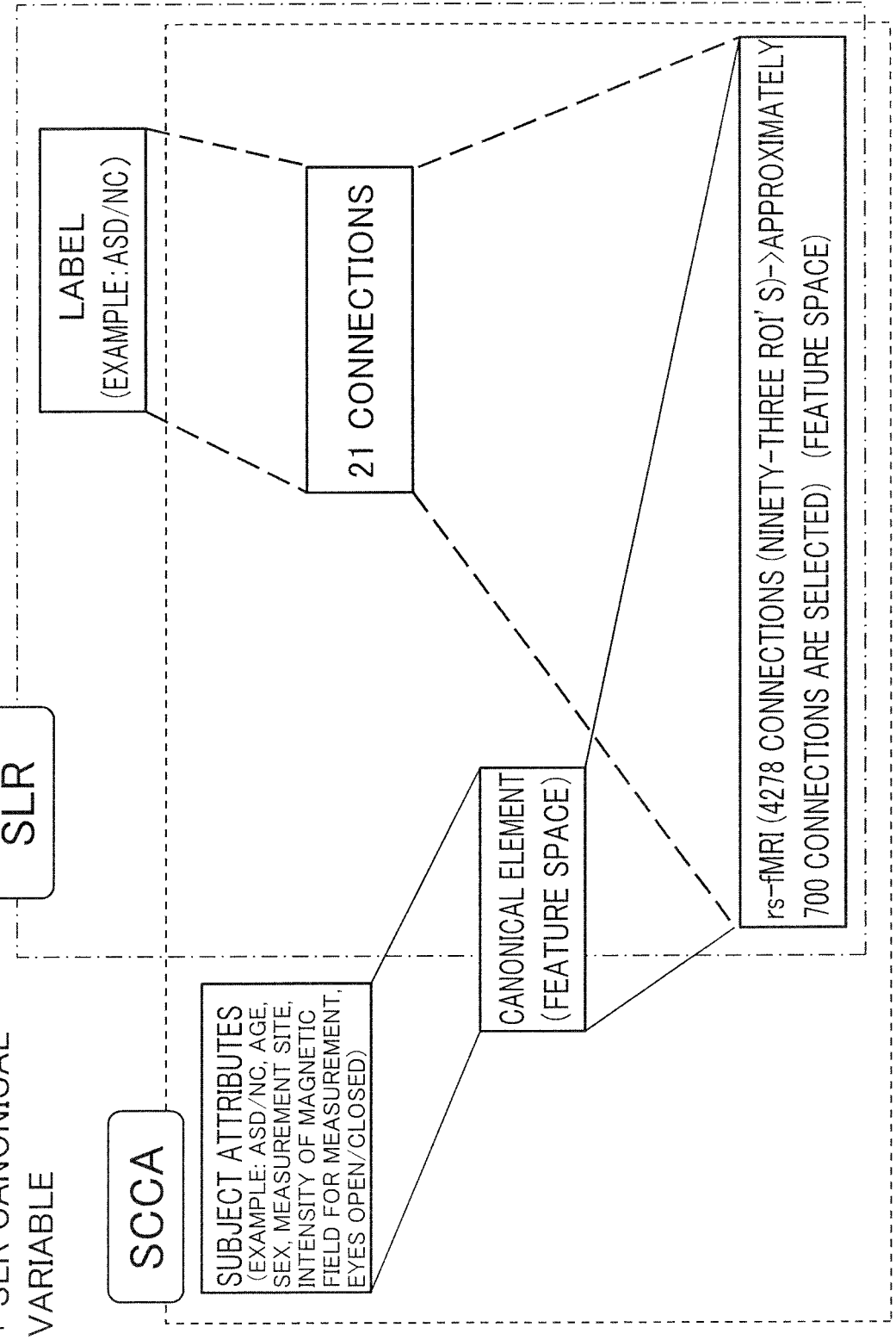
FIG. 9 shows features (SCCA feature space) obtained by SCCA and a concept of a procedure for generating the discriminator using by SLR using the features as an input.

FIGS. 7 to 9 show a concept of a procedure for generating the discriminator using features obtained by SCCA (SCCA feature space) and SLR using the features as an input.

First, as shown in FIG. 7, as a first method, using healthy/disease label as an attribute of subjects, SCCA is executed between the label and the elements of correlation matrix obtained from rs-fcMRI.

The resulting features (intermediate expression) $z_1=w_1x_1$ (canonical variance, two dimensions) are used as an input to SLR, and the discriminator is generated (hereinafter this procedure will be referred to as "method A").

Here, "canonical variance, two dimensions" means that two dimensional vectors of disease (1, 0) and healthy (0, 1) are used.

Here, of 4278 of non-diagonal elements of correlation matrix, approximately 700 elements (connections) are selected by SCCA.

Specifically, using certain data of disease/healthy diagnosis results, parameters of discriminator are determined in advance by machine learning such as SCCA, SLR or the like. The determined parameters are generalized for unknown rs-fcMRI data, and thus, the discriminator functions as a biomarker. For the discriminator, linear sum of selected connections of rs-fcMRI is applied as an input, and the disease label (1, 0) and the healthy label (0, 1) correspond to the output.

Referring to FIG. 8, as the second method, the following procedure may be adopted. Attributes of subjects include the disease/healthy label, age of the subject, sex of the subject, measurement agency (the place where the measuring apparatus is placed, referred to as measurement site: in the example described later, the number of measurement sites is three), intensity of magnetic field applied by the fMRI apparatus (corresponding to one of the indexes of performance such as the resolution of imaging apparatus), and conditions of experiments such as eyes opened/closed at the time of imaging are used. SCCA is executed between these attributes and the elements of correlation matrix obtained from rs-fcMRI. As the index of performance of fMRI imaging apparatus, not only the intensity of applied magnetic field but also other indexes may be used.

In other words, as the "explanatory variables" of canonical correlation analysis, independent elements of correlation matrix from rs-fcMRI are adopted, and as the "criterion variables," the attributes of subject such as described above are adopted.

The resulting features (intermediate expression) $z_1-w_1x_1$ (canonical variance, eleven dimensions) are used as an input to SLR, and the discriminator is generated (hereinafter this procedure will be referred to as "method B").

Here, "canonical variance, eleven dimensions" means a sum of eleven dimensions including disease/healthy (two dimensions), three sites (three dimensions: (1, 0, 0), (0, 1, 0), (0, 0, 1)), age (one dimension), sex (two dimensions (1, 0). (0, 1)), performance (one dimension), eyes opened/closed (two dimensions: (1, 0), (0, 1)).

FIG. 9 shows a third method. In the third method, as attributes of subjects, the disease/healthy label, age of the subject, sex of the subject, measurement agency (measurement site), performance of fMRI apparatus (example: intensity of magnetic field applied), and conditions of experiments such as eyes opened/closed at the time of imaging are used. SCCA is executed between these attributes and the elements of correlation matrix obtained from rs-fcMRI. This procedure is the same as method B.

Sparsely selected non-diagonal elements of rs-fcMRI as the result of SCCA are used as the input of SLR, and thus the discriminator is generated (in the following, this procedure will be referred to as "method C").

Here, in SCCA, only the non-diagonal elements of correlation matrix of rs-fcMRI related to the disease/healthy label are selected. This process filters out rs-fcMRI data expressing other factors, and thus, a biomarker independent of the agency where the data is obtained can be obtained.

By performing SCCA using influences of different sites, experimental conditions and the like, it becomes possible to find which connection is related to which factor. Therefore, it becomes possible to exclude connections unrelated to the disease/healthy label, and to derive only the connections related to the disease/healthy label. This advantageously leads to "generalization" of the biomarker.

Further, by sparse method of SLR, for example, of approximately 700 connections made sparse by SCCA, twenty-one connections are used for the discriminator by the method C.

In methods B and C described above, attributes to the subject may include a label indicating whether or not a prescribed medicine has been administered, or information of dosage or duration of administration of such medicine.

Figure 10:
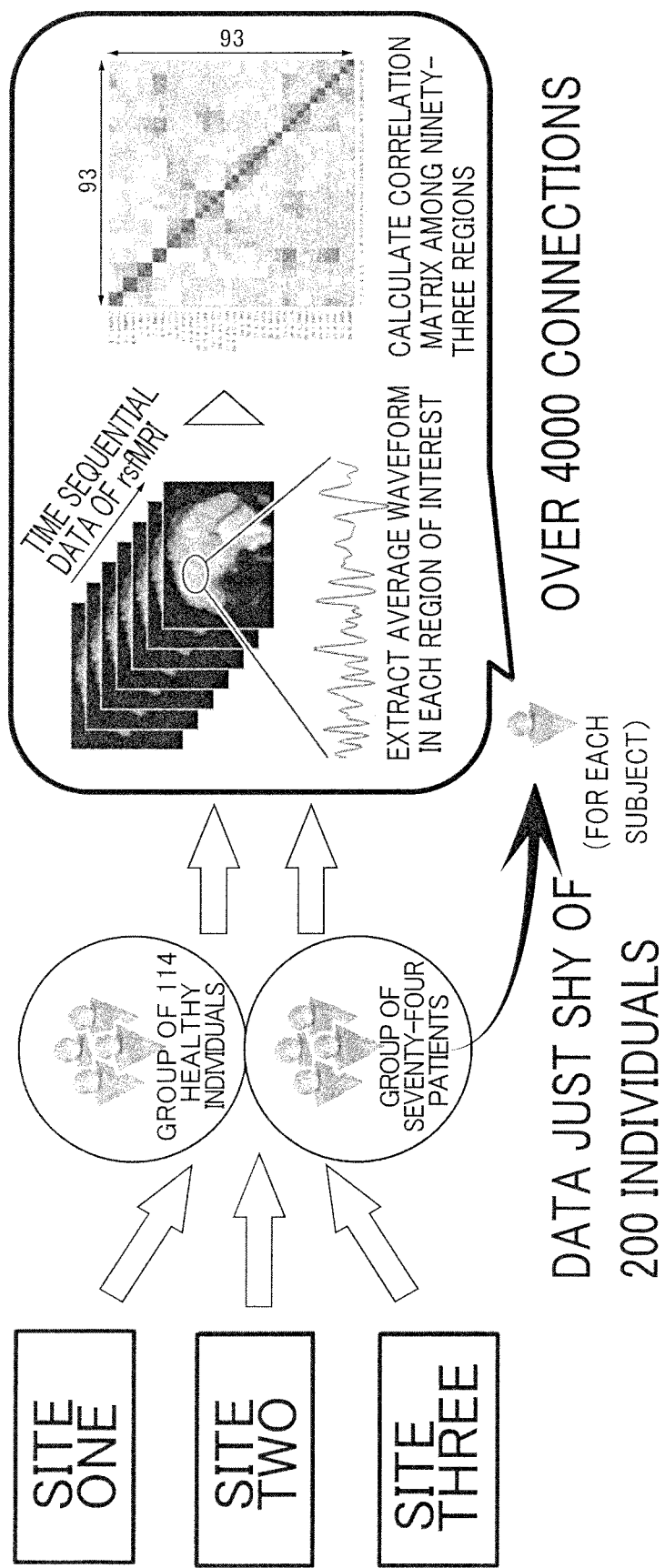
FIG. 10 shows a concept of generating a biomarker.

FIG. 10 shows a concept of such a procedure for generating the biomarker.

At three measurement agencies of Site one to Site three, using MRI apparatuses having different measurement performances, rs-fcMRI data of the group of 114 healthy individuals and the group of seventy-four patients were obtained, and from the resulting correlation matrix having more than 4000 connections, the discriminator is generated by the SCCA and SLR processes.

(Verification of Biomarker)

Figure 11:
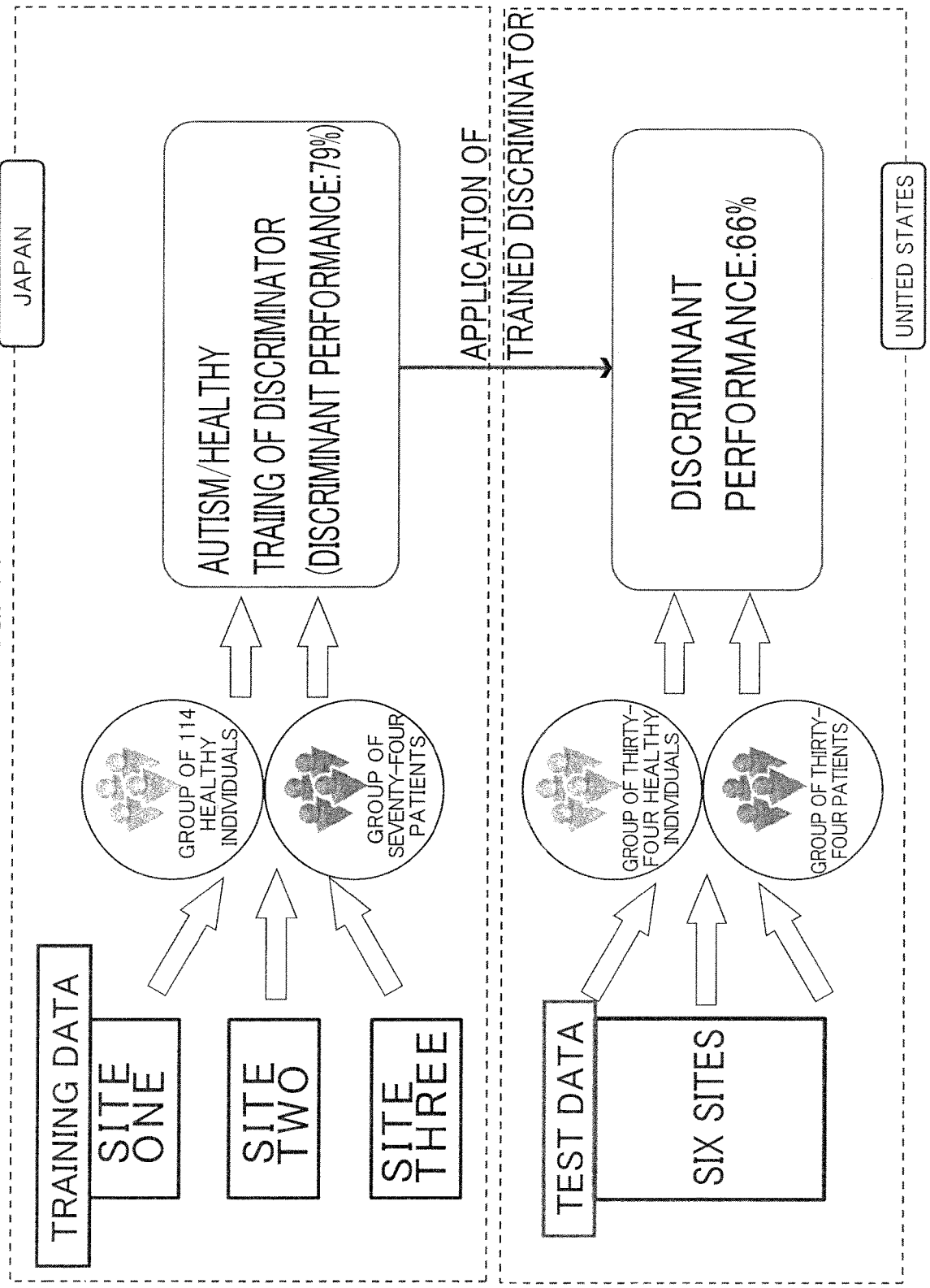
FIG. 11 shows a concept of verifying the generated biomarker.

FIG. 11 shows a concept of the procedure for verifying the biomarker generated in the manner as described above.

Using the parameters for feature extraction and discriminant obtained by learning based on the data collected at Sites one to three in Japan, disease/healthy label is predicted for the data not used for the parameter learning, and consistency with the actual disease discriminant label is evaluated.

FIG. 12 shows properties of the biomarker.

As a result of consistency evaluation mentioned above, by way of example, when method C described above was used, the discriminant performance of 79% or higher at the highest was observed for the data of three different sites in Japan. When the biomarker using the same parameter was evaluated with the rs-fcMRI data measured at six sites in the United States, the discriminant performance was 66% or higher.

In FIG. 12, Site four collectively represents the six sites in the United States.

In FIG. 12, "sensitivity" refers to the probability of correctly testing positive (having the disease) the subjects having the disease, and the "specificity" refers to the probability of correctly testing negative (not having the disease) the healthy subjects. "Positive likelihood ratio" refers to the ratio of true positive to false positive, and "negative likelihood ratio" refers to the ratio of false negative to true negative. DOR is diagnostic odds ratio, representing the ratio of sensitivity to specificity.

In FIG. 12, the generalization to the sites in the United States shows the high performance of the biomarker obtained by learning from limited data of subjects, in the sense that it goes beyond the race-by-race or country-by-country diagnostic criteria.

(Multi-Disease Biomarker)

In the foregoing, among the criterion variables of SCCA, the disease/healthy level is related to one disease.

However, when labels of a plurality of diseases are used as disease labels when rs-fcMRI data is used as the explanatory variable, it is possible to use the biomarker as multi-disease biomarker.

Specifically, here, the disease labels include labels for discriminating a disease from healthy state for each of a plurality of diseases.

Figure 13:
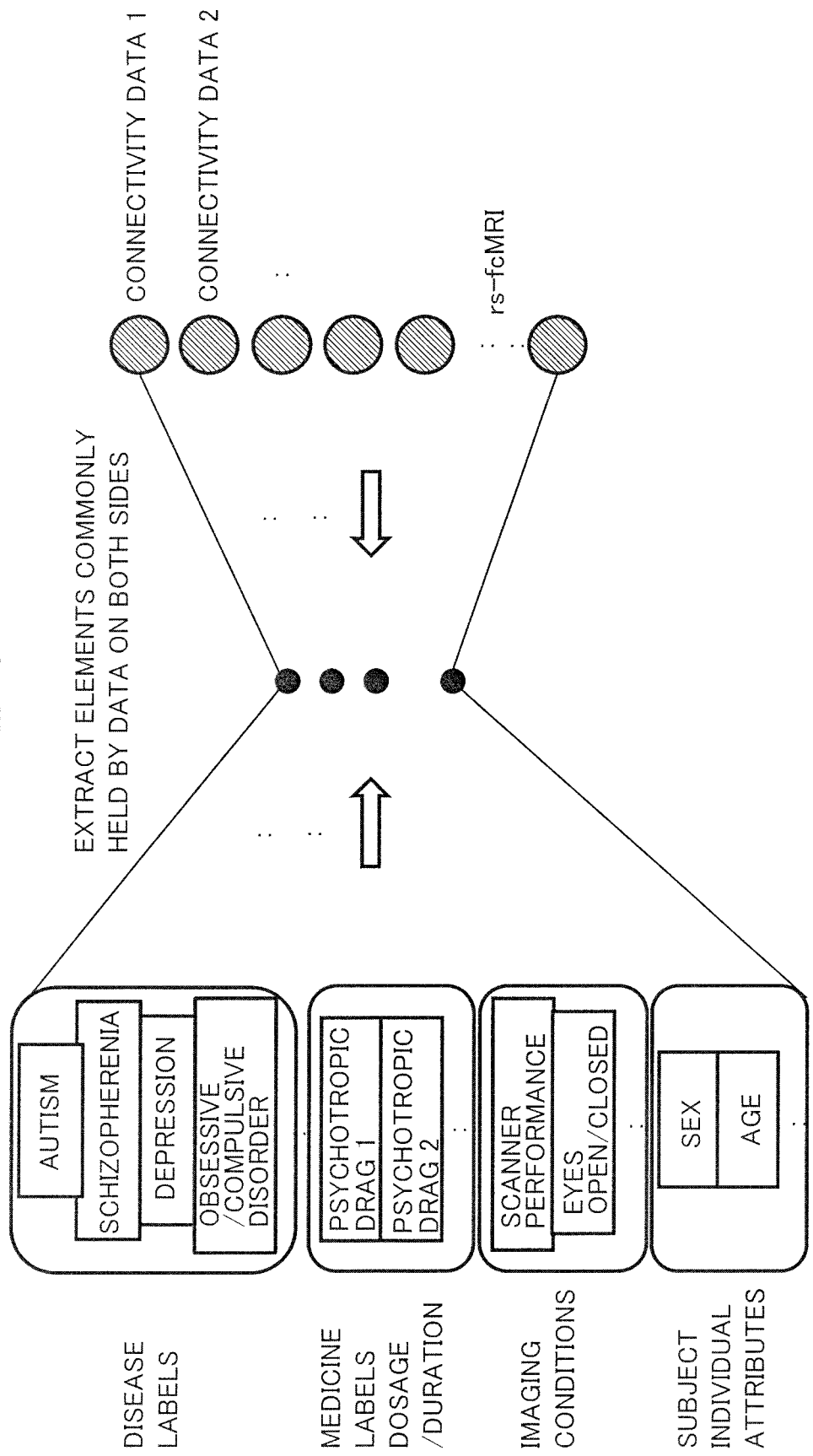
FIG. 13 shows a concept of a multi-disease biomarker.

FIG. 13 shows a concept of such a multi-disease biomarker.

FIG. 13 shows only a hypothetical example. However, if the relations among diseases that have been called by different names influences of medications and the like administered for various diseases and brain activities are studied using (SCCA+SLR) method on the rs-fcMIR data described above, it becomes possible to extract correlations between each of these.

By way of example, the disease label mentioned above may include a disease/healthy label of "autism", a disease/healthy label of "schizophrenia", a disease/healthy label of "depression" and a disease/healthy label of "obsessive/compulsive disorder."

The medication labels may include information related to types of medication such as "psychotropic drug 1" and "psychotropic drug 2" as well as dosage and administration period of each drug.

The conditions of imaging includes performance of fMRI imaging apparatus as described above (example: intensity of applied magnetic field) and information related to whether measurement was done with eyes of the subject opened/closed.

Further, individual attributes of a subject include information related to age, sex and the like.

In the foregoing description, it is assumed that real-time fMRI is used as the brain activity detecting apparatus for time-sequentially measuring brain activities by functional brain imaging. It is noted, however, that any of the fMRI described above, a magnetoencephalography, a near-infrared spectroscopy (NIRS), an electroencephalography or a combination of any of these may be used as the brain activity detecting apparatus. Regarding such a combination, it is noted that fMRI and NIRS detect signals related to change in blood flow in the brain, and have high spatial resolution. On the other hand, magnetoencephalography and electroencephalography are characterized in that they have high temporal resolution, for detecting change in electromagnetic field associated with the brain activities. Therefore, if IMRI and the magnetoencephalography are combined, brain activities can be measured with both spatially and temporally high resolutions. Alternatively, by combining NIRS and the electroencephalography, a system for measuring brain activities with both spatially and temporally high resolutions can also be implemented in a small, portable size.

By the configuration as described above, it becomes possible to realize a brain function analyzing apparatus and a brain function analyzing method functioning as biomarkers using functional brain imaging, in relation to neurological/mental disorder.

In the foregoing, an example has been described in which a "disease discriminant label" is included as an attribute of a subject, and by generating a discriminator through machine learning, the discriminator is caused to function as a biomarker. The present invention, however, is not necessarily limited to such an example. Provided that a group of subjects whose results of measurements are to be obtained as the object of machine learning is classified into a plurality of classes in advance by an objective method, the correlation of degree of activity (connectivity) among brain regions (regions of interest) of the subjects is measured and a discriminator can be generated for classification by machine learning using the measured results, the present invention may be used for other discrimination.

Further, as described above, such discrimination may indicate possibility of belonging to a certain attribute, as a probability.

Therefore, whether a certain "training" or a "behavioral pattern" is helpful to increase health of a subject or not can objectively be evaluated. Even when a subject does not yet have a disease (in as state "before the onset of a disease"), it is possible to objectively evaluate whether substance to be ingested such as "food" and "drink" or a certain activity is effective to attain a healthier state.

If an indication such as "probability of how healthy you are: ○○%" is given in the state before the onset of a disease mentioned above, it is possible to indicate the user of his/her health conditions by an objective numerical value. Here, the output need not be the probability, and "continuous value representing the degree of how healthy you are, for example, probability of being healthy" converted to a score may be displayed. By such a display, the embodiment of the present invention can be used not only as a support for diagnosis but also as an apparatus for health management.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

REFERENCE SIGNS LIST 2 subject, 6 display, 10 MRI apparatus, 11 magnetic field applying mechanism. 12 static magnetic field generating coil, 14 magnetic field gradient generating coil. 16 RF irradiating unit, 18 bed, 20 receiving coil, 21 driving unit, 22 static magnetic field power source. 24 magnetic field gradient power source, 26 signal transmitting unit, 28 signal receiving unit, 30 bed driving unit, 32 data processing unit, 36 storage unit, 38 display unit, 40 input unit, 42 control unit, 44 interface unit, 46 data collecting unit, 48 image processing unit, 50 network interface.

The invention claimed is:

1. A brain activity analyzing method for a computer including a processor and a storage device to analyze brain activity signals indicating brain activities, comprising:

receiving the brain activity signals indicating brain activities and measured in a time-series by a brain activity detecting apparatus, said brain activity signals being indicative of brain activities in a resting state at a plurality of prescribed regions in a brain of each of a plurality of first subjects;

storing brain activity data representing the brain activity signals indicative of brain activity at a plurality of prescribed regions in a brain of each of the plurality of first subjects;

calculating a correlation matrix of activities at said plurality of prescribed regions from the brain activity signals measured by said brain activity detecting apparatus, based on brain activity signals from a first set of subjects corresponding to the plurality of first subjects with a disease label and a second set of subjects with a healthy label;

selecting a first set of functional connections associated with the disease label shared by said plurality of first subjects by applying a regularized canonical correlation analysis to the brain activity data indicative of brain activities of said plurality of first subjects, between attributes of said first subjects including said disease label and non-diagonal elements of said correlation matrix;

generating a model for discriminating the disease label by extracting a second set of functional connections from the selected first set of functional connections by applying a sparse estimation algorithm to the first set of functional connections; and storing information for specifying said model in said storage device, wherein the model for discriminating extracts the second set of functional connections from the selected first set of functional connections, by extracting a contraction expression common to said attributes of said plurality of first subjects, from among correlations of the brain activity data indicative of brain activities of said plurality of first subjects, and wherein the model for discriminating includes one or more discriminators and is useable to predict the presence of a mental disorder associated with the disease label.

2. The brain activity analyzing method of claim 1 wherein the model is used to predict a disease label of a new subject through the execution of the model on the brain activity data indicative of brain activities at a plurality of prescribed regions in a brain of the new subject.

3. The brain activity analyzing method according to claim 1, wherein said processor generates the model by sparse logistic regression on a result of said regularized canonical correlation analysis and the disease label of said first subjects.

4. The brain activity analyzing method according to claim 1, wherein said attributes of said first subjects include a label of a medicine administered to the subjects.

5. The brain activity analyzing method according to claim 1, wherein
said brain activity detecting apparatus includes a plurality of brain activity measuring devices; and
said generating includes
extracting said first set of functional connections related to said disease label independently of conditions for measurement of said plurality of brain activity measuring devices, by variable selection from correlations of brain activities at said plurality of prescribed regions.

* * * * *